US 8,305,581 B2

(12) United States Patent
Anderson et al.

(10) Patent No.: US 8,305,581 B2
(45) Date of Patent: *Nov. 6, 2012

(54) METHODS AND APPARATUS FOR ANALYZING SAMPLES AND COLLECTING SAMPLE FRACTIONS

(75) Inventors: James Anderson, Arlington Heights, IL (US); Raaidah Saari-Nordhaus, Antioch, IL (US); Washington Mendoza, Lake in the Hills, IL (US); Josef Bystron, Chicago, IL (US); Dirk Helgemo, Shakopee, MN (US); Dennis McCreary, Greencastle, PA (US)

(73) Assignee: Alltech Associates, Inc., Columbia, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/960,042

(22) Filed: Dec. 3, 2010

(65) Prior Publication Data

US 2011/0310390 A1    Dec. 22, 2011

Related U.S. Application Data

(62) Division of application No. 12/529,477, filed on Sep. 1, 2009, now Pat. No. 8,115,930.

(51) Int. Cl.
*G01N 21/00* (2006.01)
(52) U.S. Cl. ........................ 356/436; 356/440
(58) Field of Classification Search ........... 356/432–442
See application file for complete search history.

(56) References Cited

U.S. PATENT DOCUMENTS

| | | | |
|---|---|---|---|
| 3,694,085 A | 9/1972 | Rich | 356/37 |
| 3,700,333 A | 10/1972 | Charleson et al. | 356/103 |
| 3,738,751 A | 6/1973 | Rich | 356/37 |
| 3,787,123 A | 1/1974 | Sigrist | 356/103 |
| 3,806,248 A | 4/1974 | Sinclair | 356/37 |
| 3,975,946 A | 8/1976 | Ball et al. | 73/61.1 |
| 4,066,411 A | 1/1978 | Fine et al. | 23/253 |
| 4,112,297 A | 9/1978 | Miyagi et al. | 250/288 |
| 4,293,217 A | 10/1981 | Bird, Jr. et al. | 356/37 |
| 4,357,420 A | 11/1982 | Bostick et al. | 435/8 |
| 4,565,446 A | 1/1986 | Chu | 356/246 |
| 4,748,377 A | 5/1988 | King | 315/3.5 |
| 4,775,481 A | 10/1988 | Allington | 210/656 |
| 4,883,958 A | 11/1989 | Vestal | 250/288 |
| 4,894,529 A | 1/1990 | Borden et al. | 250/222.2 |
| 4,940,327 A | 7/1990 | Lilienfeld | 356/338 |
| 4,958,529 A | 9/1990 | Vestal | 73/864.81 |
| 5,030,002 A | 7/1991 | North, Jr. | 356/73 |
| 5,033,541 A | 7/1991 | D'Silva | 165/155 |
| 5,227,135 A | 7/1993 | Godec et al. | 422/98 |

(Continued)

FOREIGN PATENT DOCUMENTS

EP        1380329        1/2004

(Continued)

OTHER PUBLICATIONS

U.S. Appl. No. 12/959,933, filed Nov. 3, 2010, Anderson, James et al.

(Continued)

*Primary Examiner* — Tara S Pajoohi Gomez
(74) *Attorney, Agent, or Firm* — William D. Bunch

(57) ABSTRACT

Methods and apparatus for analyzing a sample using at least one detector are disclosed.

20 Claims, 13 Drawing Sheets

U.S. PATENT DOCUMENTS

| | | | | |
|---|---|---|---|---|
| 5,234,586 | A | 8/1993 | Afeyan et al. | 210/198.2 |
| 5,306,426 | A | 4/1994 | Afeyan | 210/635 |
| 5,538,643 | A | 7/1996 | Kallos et al. | 210/656 |
| 5,814,128 | A | 9/1998 | Jiang et al. | 95/82 |
| 6,106,710 | A | 8/2000 | Fischer et al. | 210/198.2 |
| RE36,892 | E | 10/2000 | Apffel, Jr. et al. | 250/288 |
| 6,183,635 | B1 | 2/2001 | Klee et al. | 210/198.2 |
| 6,229,605 | B1 | 5/2001 | Benedict | 356/339 |
| 6,289,914 | B1 | 9/2001 | Tommasi | 137/15.18 |
| 6,294,087 | B1 | 9/2001 | Hargro et al. | 210/198.2 |
| 6,362,880 | B1 | 3/2002 | Anderson, Jr. et al. | 356/337 |
| 6,377,341 | B1 | 4/2002 | Rowlen et al. | 356/128 |
| 6,406,633 | B1 | 6/2002 | Fischer et al. | 210/659 |
| 6,436,292 | B1 | 8/2002 | Petro | 210/656 |
| 6,461,515 | B1 | 10/2002 | Safir et al. | 210/656 |
| 6,568,245 | B2 | 5/2003 | Kaufman | 73/28.02 |
| 6,627,075 | B1 | 9/2003 | Weissgerber et al. | 210/198.2 |
| 6,707,035 | B2 | 3/2004 | Hughey et al. | 250/288 |
| 6,712,085 | B2 | 3/2004 | Weissgerber et al. | 137/12 |
| 6,730,228 | B2 | 5/2004 | Petro et al. | 210/656 |
| 6,767,467 | B2 | 7/2004 | Fischer et al. | 210/659 |
| 6,776,902 | B2 | 8/2004 | Petro | 210/198.2 |
| 6,855,258 | B2 | 2/2005 | Petro et al. | 210/656 |
| 6,867,415 | B2 | 3/2005 | Hughey et al. | 250/288 |
| 6,890,489 | B2 | 5/2005 | Nichols et al. | 422/103 |
| 6,984,524 | B2 | 1/2006 | Nguyen et al. | 436/107 |
| 6,989,129 | B2 | 1/2006 | Licklinder et al. | 422/70 |
| 7,006,218 | B2 | 2/2006 | Anderson, Jr. et al. | 356/337 |
| 7,129,479 | B2 | 10/2006 | Caroll et al. | 250/287 |
| 7,169,308 | B2 | 1/2007 | Ohkura | 210/656 |
| 7,214,320 | B1 | 5/2007 | Gregori et al. | 210/656 |
| 7,267,796 | B2 | 9/2007 | Waki | 422/70 |
| 7,290,723 | B1 | 11/2007 | Lu et al. | 239/135 |
| 7,318,900 | B2 | 1/2008 | DeMarco | 210/656 |
| 7,419,598 | B2 | 9/2008 | Davison | 201/604 |
| 7,429,731 | B1 | 9/2008 | Karpetsky | 250/288 |
| 7,575,723 | B2 | 8/2009 | Nichols et al. | 422/103 |
| 7,686,959 | B2 | 3/2010 | Horsman et al. | 210/656 |
| 7,901,628 | B2 | 3/2011 | Yamamoto | 422/70 |
| 2001/0013494 | A1 | 8/2001 | Maiefski et al. | 210/656 |
| 2001/0038071 | A1 | 11/2001 | Nichols et al. | 250/288 |
| 2002/0121468 | A1 | 9/2002 | Fischer et al. | 210/198.2 |
| 2002/0146349 | A1 | 10/2002 | Gygi et al. | 422/70 |
| 2002/0190001 | A1 | 12/2002 | Miroslav | 210/656 |
| 2003/0080062 | A1 | 5/2003 | Petro et al. | 210/656 |
| 2003/0089663 | A1 | 5/2003 | Petro et al. | 210/656 |
| 2003/0224390 | A1* | 12/2003 | Fowlkes et al. | 435/6 |
| 2005/0175683 | A1 | 8/2005 | Zhang | 424/450 |
| 2005/0226778 | A1 | 10/2005 | Houser et al. | 422/99 |
| 2005/0239152 | A1 | 10/2005 | Irth et al. | 435/8 |
| 2006/0075806 | A1 | 4/2006 | Gilby et al. | 73/61.57 |
| 2006/0085139 | A1 | 4/2006 | Collette et al. | 702/20 |
| 2006/0093521 | A1 | 5/2006 | Swartz et al. | 422/70 |
| 2006/0192108 | A1 | 8/2006 | Yeatman et al. | 250/288 |
| 2006/0219637 | A1 | 10/2006 | Kileen et al. | 210/656 |
| 2006/0238744 | A1 | 10/2006 | O'Donohue | 356/37 |
| 2006/0285108 | A1 | 12/2006 | Morrisroe | 356/316 |
| 2007/0023037 | A1 | 2/2007 | Larsen et al. | 128/200.18 |
| 2007/0056357 | A1 | 3/2007 | Ruegenberg et al. | 73/53.01 |
| 2007/0089493 | A1 | 4/2007 | Alington et al. | 73/61.52 |
| 2007/0122314 | A1 | 5/2007 | Strand et al. | 422/100 |
| 2007/0132229 | A1 | 6/2007 | Mueller et al. | 285/124.2 |
| 2007/0181505 | A1* | 8/2007 | DeMarco | 210/656 |
| 2008/0144003 | A1 | 6/2008 | Blackford et al. | 356/37 |
| 2008/0186489 | A1 | 8/2008 | Ahn | 356/337 |
| 2010/0238444 | A1 | 9/2010 | Anderson et al. | 356/436 |
| 2011/0017670 | A1 | 1/2011 | Anderson et al. | 210/656 |

FOREIGN PATENT DOCUMENTS

| | | |
|---|---|---|
| EP | 1370571 | 6/2005 |
| EP | 01707957 | 10/2006 |
| EP | 1348958 | 9/2008 |
| WO | 9925451 | 5/1999 |
| WO | 9925452 | 5/1999 |
| WO | 0026662 | 5/2000 |
| WO | 0037157 | 6/2000 |
| WO | 0045929 | 8/2000 |
| WO | 0136071 | 5/2001 |
| WO | 02063291 | 8/2002 |
| WO | 02082071 | 10/2002 |
| WO | 03008101 | 1/2003 |
| WO | 03021251 | 3/2003 |
| WO | 2005116628 | 12/2005 |
| WO | 2006042365 | 4/2006 |
| WO | 2008070776 | 6/2008 |
| WO | 2008118808 | 10/2008 |
| WO | 2009075764 | 6/2009 |

OTHER PUBLICATIONS

U.S. Appl. No. 12/960,114, filed Dec. 3, 2010, Anderson, James et al.
U.S. Appl. No. 13/132,619, filed Jun. 3, 2011, Olsen, Kristine et al.
U.S. Appl. No. 13/133,733, filed Jun. 9, 2011, Anderson, James et al.
U.S. Appl. No. 13/133,837, filed Jun. 9, 2011, Saari-Nordhaus, Raaidah et al.
U.S. Appl. No. 13/139,016, filed Jun. 10, 2011, Bystron, Josef et al.
U.S. Appl. No. 13/139,030, filed Jun. 10, 2011, Bystron Josef, et al.
U.S. Appl. No. 13/139,061, filed Jun. 10, 2011, Saari-Nordhaus, Raaidah.
U.S. Appl. No. 13/262,756, filed Oct. 3, 2011, McCreary Dennis et al.
U.S. Appl. No. 13/266,870, filed Oct. 28, 2011, Saari-Nordhaus, Raaidah et al.
Automated Semipreparative Purification with Mass Spectrometric Fraction Collection Trigger: Modeling and Experimental Evaluation of a Setup Employing Passive Splitting by Steiner, F., Mahsunah A., Arnold F., Piecha T., Huber C.; J. Sep. Sci 2007, 30, 1496-1508.
Blue Natural Organic Dyestuffs—From Textile Dyeing to Mural Painting. Separation and Characterization of Coloring Matters Present in Elderberry, Logwood and Indigo by Pawlak, K., Puchalska, M., Miszczak, A., Rostoniec, E., and Jarosz, M.,; Journal of Mass Spectrometry 2006; 41: 613-622.
High-Throughput Purification of Combinatorial Libraries I: A High-Throughput Purification System Using an Acclerated Retention Window Approach by Yan, B., Collins, N., Wheatley, J., Irving, M., Leopold, K., Chan, C., Shornikov, A., Fang, L., Lee, A., Stock, M., and Zhao, J.; J. Comb Chem. 2004, 6, 255-261.
On-Line Mass Characterization of Fractions in a Multi-Channel Preparitive HPLC Environment by Liu, J., Bickler, J., Rahn, P.C., R & D Biotage, Inc.; Abstracts of Papers American Chemical Society, vol. 223 (2002).
Optimal Fraction Collecting in Preparative LC/MS by Rosentreter, U. and Huber, U.; Journal of Combinatorial Chemistry, vol. 6, No. 2, 2004.
Purification of Alkaloids from Corydalis Yanhusuo W.T. Wang Using Preparative 2-D HPLC by Zhang, Jing; Jin, Yu; Liu, Yanfang; Xiao, Yuansheng; Feng, Jiatao; Xue, Xingya; Zhang, Xiuli; Liang, Xinmiao; J. Sep. Sci. 2009, 31, 1401-1406.
Quantification of fipronil and its metabolite fipronil sulfone in rat plasma over a wide range of concentrations by LC/UV/MS by Lacroix, M Z; Puel, S; Toutain, P L; Viguioe, C.; J Chromatogr B Analyt Technol Biomed Life Sci vol. 878, No. 22, Jul. 15, 2012.
Role of mass spectrometry in the purification of peptides and proteins by Mazza, C. B.; Cavanaugh, J. Y.; Neue, U. D.; Phillips, D. J.; J. Chromatogr. B Anal. Technol. Biomed. Life Sci vol. 790, Jun. 25, 2003.
Sample preparation for hyphenated analytical techniques by Rosenfeld, J.M.; p. 121-123, 2004.
Separation and Identification of Compounds in Adinandra Nitida by Comprehensive Two-Dimensional Liquid Chromatography Coupled to Atmospheric Pressure Chemical Ionization Source Ion Trap Tandem Mass Spectrometry by J. Zhang, D. Tao, J. Duan, Z. Liang, W. Zhang, L. Zhang, Y. Huo, and Y. Zhang. From Anal Bioanal Chem (2006) 386: 586-593.
On-Line Sample Enrichment System Coupled to Electrospray Ionization Time-of-Flight Mass Spectrometry (ESI-TOF-MS) by M. Okamoto, K. Yamashita, and K. Nakai from Journal of Pharmaceutical and Biomedical Analysis 41 (2006) 707-713.
Liquid Chromatography with Ultraviolet Absorbance-Mass Spectrometric Detection and with Nuclear Magnetic Resonance Spectroscopy: A Powerful Combination for the On-Line Structural Investigation of Plant Metabolites by J. Wolfender, K Ndjoko, and K Hostettmann from Journal of Chromatography A, 1000 (2003) 437-455.

A Straightforward Means of Coupling Preparative High-Perfromance Liquid Chromatography and Mass Spectrometry by H. Cai, J. Kiplinger, W. Goetzinger, R. Cole, K. Laws, M. Foster, and A Schrock from Rapid Communications in Mass Spectrometry (2002) 16: 544-554.

A novel hyphenated LC-ARC-RD-MS-FC system for identification of drug metabolites; Proceedings of the 50th ASMS Conference on Mass Spectrometry and Allied Topics, Orlando Florida, Jun. 2-6, 2002 by Wenzhe Lu, ChungPing Yu, Dian Y. Lee.

Analysis of Rhubarb by Liquid Chromatography-Electrospray-Mass Spectrometry; Tamkang Journal of Science and Engineering, Vik. 6, No. 1, pp. 31-36 (2003) by Ming-Ren S. Fuh and Hung-Jian Lin.

Automated simultaneous isolation and quantitation of labeled amino acid fractions from plasma and tissue by ion-exchange chromatography; Journal of Chromatography B, 660 (1994) 251-257 by Hans M.H. van Eijik, Mark P.L. Huinck, Dennis R. Rooyakkers, Nicolaas E.P. Deutz.

Characterization of apolipoprotein and apolipoprotein precursors in pancreatic cancer serum samples via two-dimensional liquid chromatography and mass spectrometry; Journal of Chromatography A. 1162 (2007) 117-125 by Jianzhong Chen, Michelle Anderson, David E. Misek, Diane M. Simeone, and David M Lubman.

Evaluation of applicability of the flow splitter to frit-FAB LC-MS system; Mass Spectroscopy vol. 39, No. 4, Aug. 1991 by Yoshitomo Ikai, Hisao Oka, Junko Hayakawa, Ken-ichi Harada, and Makato Suzuki.

High-Throughput Mass-Directed Parallel Purification Incorporating a Multiplexed Single Quadrupole Mass Spectrometer; Anal. Chem. 2002, 74, 3055-3062 by Rongda Xu, Tao Wang, John Isbell, Zhe Cai, Christopher Sykes, Andrew Brailsford, and Daniel B. Kassel.

Hyphenation of centrifugal partition chromatography with electrospray ionization mass spectrometry using an active flow-splitter device for characterization of flavonol glycosides; Rapid Communications in Mass Spectrometry 2009; 23; 1863-1870 by Alix Toribio, Emilie Desandau, Claire Elfakir, and Michel Lafosse.

Hyphenation of high performance liquid chromatography with sector field inductively coupled plasma mass spectrometry for the determination of ultra-trace level anionic and cationic arsenic compounds in freshwater fish; J. Anal. At. Spectrom., 2004, 19, 191-195 by Jian Zheng and Holger Hintelmann.

Identification of intact glucosinolates using direct coupling of high-performance liquid chromatography with continuous-flow frit fast atom bombardment tandem mass spectrometry; Biological Mass Spectrometry, vol. 20, 259-263 (1991) by P.S. Kokkonen, J. van der Greef W.M.A. Niessen, U.R. Tjaden, G.J. ten Hove, and G. van de Werken.

Improved liquid chromatography—mass spectrometry performance in quantitative analysis using a nanosplitter interface; Journal of Chromatography A. 1053 (2004) 151-159 by Christine L. Andrews, Chung-Ping Yu, Eric Yang, and Paul Vouros.

Novel system for separation of phospholipids by high-performance liquid chromatography; Journal of Chromatography, 234 (1982) 218-221 by Iftekhar Alam, J. Bryan Smith, Melvin J. Silver, and David Ahern.

Optimization of a liquid chromatography method based on simulataneous electrospray ionization mass spectrometric and ultraviolet photodiode array detection for analysis of flavonoid glycosides; Rapid Communications in Mass Spectometry 2002; 16: 2341-2348 by Filip Cuyckens and Magda Claeys.

Quantitation of Radiolabeled Compounds Eluting from the HPLC System; Journal of Chromatographic Science, vol. 20, Nov. 1982 by Michael J. Kessler.

Rapid analysis of antibiotic-containing mixtures from fermentation broths by using liquid chromatography-electrospray ionization-mass spectrometry and matrix-assisted laser desorption ionization-time-of-flight-mass spectrometry; American Society for Mass Spectrometry, 1996, 7, 1227-1237 by Bradley L. Ackermann, Brian T. Regg, Luigi Colombo, Sergio Stella, and John E. Coutant.

Application of a xenon arc lamp as a light source for evaporative light scattering detection; Anal Bioanal Chem (2006) 384: 1302-1307 by Karen Guadin etl al.

Enhancement of evaporative light scattering detection in high-performance liquid chromatographic determination of neomycin based on highly volatile mobile phase, high-molecular-mass ion-pairing reagents and controlled peak shape; Journal of Chromatography A 1057 (2004) 125-131 by Nikolaos C. Megoulas et al.

Search Report and Written Opinion for PCT/US2008/013359; May 27, 2010.

* cited by examiner

METHODS AND APPARATUS FOR ANALYZING SAMPLES AND COLLECTING SAMPLE FRACTIONS

CROSS REFERENCE TO RELATED APPLICATIONS

This application is a divisional of U.S. patent application Ser. No. 12/529,477 filed Sep. 1, 2009 now U.S. Pat. No. 8,115,930

FIELD OF THE INVENTION

The present invention is directed to methods and apparatus for analyzing samples and collecting sample fractions with a chromatography system.

BACKGROUND OF THE INVENTION

There is a need in the art for methods of efficiently and effectively analyzing samples and collecting sample fractions with a chromatography system. There is also a need in the art for an apparatus capable of effectively analyzing samples and collecting sample fractions.

SUMMARY OF THE INVENTION

The present invention relates to the discovery of methods for analyzing samples and collecting sample fractions with a chromatography system. The disclosed methods provide a number of advantages over known methods of analyzing samples. For example, the disclosed methods of the present invention may utilize a splitter pump or a shuttle valve to actively control fluid flow through at least one detector so that process variables (e.g., flow restrictions, total flow rate, temperature, and/or solvent composition) do not negatively impact the fluid flow through the at least one detector. The disclosed methods of the present invention may also utilize two or more detectors to provide a more complete analysis of a given sample, as well as collection of one or more sample fractions in response to one or more detector signals from the two or more detectors.

The present invention is directed to methods of analyzing samples and collecting sample fractions. In one exemplary embodiment, the method of analyzing a sample comprises the steps of generating a composite signal from two or more detectors in a liquid chromatography system, the composite signal comprising a detection response component from each detector; and collecting a new sample fraction in a fraction collector in response to a change in the composite signal. In one embodiment, the composite signal may comprise (i) a detection response component from at least one optical absorbance detector (e.g., an UV detector) and (ii) a detection response component from at least one evaporative particle detector. In one embodiment, chromophoric or non-chromophoric solvents may be utilized in the chromatography system as the carrier fluid. In another embodiment, the composite signal may comprise (i) a detection response component comprising two or more detector responses from an optical absorbance detector (e.g., an UV detector) at two or more specific optical wavelengths and (ii) a detection response component from an evaporative particle detector.

In a further exemplary embodiment according to the present invention, the method of analyzing a sample using chromatography comprises the steps of using at least one detector to observe the sample that comprises at least one non-chromaphoric analyte compound; and collecting a new sample fraction in a fraction collector in response to a change in a detector response of the non-chromaphoric compound. The sample may include numerous different chromaphoric and non-chromaphoric compounds. In addition, the mobile phase that carries the sample may include one or more chromaphoric or non-chromaphoric compounds.

In another embodiment, universal carrier fluid may be utilized in the chromatography system, including volatile liquids and various gases. In a further embodiment, a non-destructive detector (e.g., RI, UV detector, etc.) may be combined with a destructive detector (e.g., evaporative particle detector, mass spectrometer, spectrophotometer, emission spectroscopy, NMR, etc.), which enables detection of various compound specific properties of the sample, such as, for example, the chemical entity associated with the peak.

In a further exemplary embodiment, the method of analyzing a sample comprises the steps of using at least one detector to observe the sample at two or more specific optical wavelengths; and collecting a new sample fraction in a fraction collector in response to (i) a change in a detector response at a first wavelength, (ii) a change in a detector response at a second wavelength, or (iii) a change in a composite response represented by the detector responses at the first and second wavelengths. A change in a given detector response may include, but is not limited to, a change in a detector response value, reaching or exceeding a threshold detector response value, a slope of the detector response value over time, a threshold slope of the detector response value over time, a change in a slope of the detector response value over time, a threshold change in a slope of the detector response value over time, or any combination thereof. In this embodiment, the method may comprise using n sensors in at least one detector to observe n specific wavelengths across a range of an absorbance spectrum, wherein n is an integer greater than 1; and collecting a new sample fraction in the fraction collector in response to (i) a change in any one of n detector responses from the n sensors, or (ii) a change in a composite response represented by the n detector responses.

In yet a further exemplary embodiment, the method of analyzing a sample comprises the steps of providing a liquid chromatography system comprising (i) a chromatography column, (ii) a tee having a first inlet, a first outlet and a second outlet, (iii) a fraction collector in fluid communication with the first outlet of the tee, and (iv) a detector in fluid communication with the second outlet of the tee; and actively controlling fluid flow through the detector via (v) a splitter pump positioned in fluid communication with the second outlet of the tee and the detector. In other exemplary embodiments, a shuttle valve may be used in place of the tee and splitter pump to actively control fluid flow through to at least one detector. In an exemplary embodiment, the shuttle valve is a continuous flow shuttle valve with the ability to remove very small sample volumes from the sample stream.

In an even further exemplary embodiment of the present invention, a method of analyzing a sample of fluid using chromatography includes the steps of providing a first fluid of effluent from a chromatography column; providing a second fluid to carry the sample of fluid to at least one detector; using a shuttle valve to remove an aliquot sample of fluid from the first fluid and transfer the aliquot to the second fluid while maintaining a continuous path of the second fluid through the shuttle valve; using at least one detector to observe the aliquot sample of fluid; and collecting a new sample fraction of the first fluid in a fraction collector in response to a change in a detector response. In one embodiment, a continuous flow path of the first fluid through the shuttle valve is maintained when the aliquot sample of fluid is removed from the first fluid. In another embodiment, continuous flow paths of both the first fluid and the second fluid through the shuttle valve are maintained when the aliquot sample of fluid is removed from the first fluid and transferred to the second fluid.

In another exemplary embodiment according to the present invention, a method of analyzing a sample of fluid using chromatography includes the steps of providing a first fluid comprising the sample; using a shuttle valve to remove an aliquot sample of fluid from the first fluid without substantially affecting flow properties of the first fluid through the shuttle valve; using at least one detector to observe the aliquot sample of fluid; and collecting a new sample fraction of the first stream in a fraction collector in response to a change in at least one detector response. The flow of the first fluid through the shuttle valve may be substantially laminar, due to the first fluid path or channel being substantially linear or straight through at least a portion of the valve. In a further exemplary embodiment, the pressure of the first fluid through the shuttle valve remains substantially constant and/or it does not substantially increase. In another embodiment, the flow rate of the first fluid may be substantially constant through the shuttle valve. In an alternative embodiment, a second fluid is utilized to carry the aliquot sample of fluid from the shuttle valve to the detector(s). The flow of the second fluid through the shuttle valve may be substantially laminar due to the second fluid path or channel being substantially linear or straight through at least a portion of the valve. In an exemplary embodiment, the pressure of the second fluid through the shuttle valve is substantially constant and/or it does not substantially increase. In another embodiment, the flow rate of the second fluid may be substantially constant through the shuttle valve.

In a further exemplary embodiment, the method of analyzing a sample comprises the steps of providing a non-destructive system liquid chromatography system comprising (i) a chromatography column, (ii) two or more non-destructive detectors (e.g., an optical absorbance detector such as a UV detector) with no destructive detectors (e.g., a mass spectrometer) present in the system, and (iii) a fraction collector in fluid communication with the two or more non-destructive detectors; and collecting one or more sample fractions in response to detector signals from the two or more non-destructive detectors.

In another exemplary embodiment according to the present invention, a method of analyzing a sample using flash chromatography includes the steps of using an evaporative particle detector to observe the sample that is capable of detecting individual compounds; and collecting a new sample fraction in a fraction collector in response to a change in a detector response of the compound, wherein the evaporative particle detector is the only detector utilized to analyze the sample. The evaporative particle detector is capable of detecting chemical composition, chemical structure, molecular weight, or other chemical or physical properties. The detector may include an ELSD, CNLSD or mass spectrometer.

In yet a further exemplary embodiment, the method of analyzing a sample comprises the steps of generating a detector signal from at least one detector in a liquid chromatography system, the detector signal being generated in response to (i) the slope of a detector response as a function of time (i.e., the first derivative of a detector response), (ii) a change in the slope of the detector response as a function of time (i.e., the second derivative of the detector response), (iii) optionally, reaching or exceeding a threshold detector response value, or (iv) any combination of (i) to (iii) desirably comprising at least (i) or at least (ii); and collecting one or more sample fractions in response to at least one detector signal from the at least one detector.

In yet another exemplary embodiment, the method of analyzing a sample comprises the step of collecting a sample fraction in a fraction collector of a liquid chromatography system, wherein the fraction collector is operatively adapted to (i) recognize, receive and process one or more signals from at least one detector, and (ii) collect one or more sample fractions based on the one or more signals.

The present invention is also directed to an apparatus capable of analyzing a sample. In one exemplary embodiment, the apparatus for analyzing a sample comprises system hardware operatively adapted to generate a composite signal from two or more detectors in a liquid chromatography system, the composite signal comprising a detection response component from each detector; and a fraction collector operatively adapted to collect a new sample fraction in response to a change in the composite signal.

In another exemplary embodiment, the apparatus for analyzing a sample comprises at least one detector operatively adapted to observe two or more specific optical wavelengths (e.g., UV wavelengths); and a fraction collector operatively adapted to collect a new sample in response to (i) a change in a detector response at a first wavelength, (ii) a change in a detector response at a second wavelength, or (iii) a change in a composite response represented by the detector responses at the first and second wavelengths. As discussed above, a change in a given detector response may include, but is not limited to, a change in a detector response value, reaching or exceeding a threshold detector response value, a slope of the detector response value over time, a threshold slope of the detector response value over time, a change in a slope of the detector response value over time, a threshold change in a slope of the detector response value over time, or any combination thereof.

The at least one detector may together comprise n sensors to observe n specific wavelengths across a range of an absorbance spectrum, wherein n is an integer greater than 1, and the fraction collector is operatively adapted to collect a new sample in response to (i) a change in any one of n detector responses from the n sensors, or (ii) a change in a composite response represented by the n detector responses. In one embodiment, the apparatus comprises a single UV detector comprising n sensors alone or in combination with one or more additional detectors.

In yet a further exemplary embodiment, the apparatus for analyzing a sample comprises system hardware that enables generation of a detector signal from at least one detector in a liquid chromatography system, the detector signal being generated in response to (i) the slope of a detector response as a function of time (i.e., the first derivative of a detector response), (ii) a change in the slope of the detector response as a function of time (i.e., the second derivative of the detector response), (iii) optionally, reaching or exceeding a threshold detector response value, or (iv) any combination of (i) to (iii) desirably comprising at least (i) or at least (ii). The apparatus may further comprise a fraction collector operatively adapted to collect one or more sample fractions in response to the detector signal from the at least one detector.

In another exemplary embodiment according to the present invention, an apparatus for analyzing a sample using chromatography includes at least one detector that are capable of detecting chromaphoric and non-chromaphoric analyte compounds in the sample; and a fraction collector that is capable of responding to a change in a detector response of the non-chromaphoric compound. The sample may include numerous different chromaphoric and non-chromaphoric compounds. In addition, the mobile phase that carries the sample may include one or more chromaphoric or non-chromaphoric compounds.

In yet a further exemplary embodiment, the apparatus for analyzing a sample comprises (i) a chromatography column; (ii) a tee having a first inlet, a first outlet and a second outlet; (iii) a fraction collector in fluid communication with the first outlet of the tee; (iv) a first detector in fluid communication with the second outlet of the tee; and (v) a splitter pump positioned in fluid communication with the second outlet of the tee and the first detector, the splitter pump being operatively adapted to actively control fluid flow through the first detector. In other exemplary embodiments, a shuttle valve may be used in place of the tee and splitter pump to actively control fluid flow through to at least one detector. In an exemplary embodiment, the shuttle valve is a continuous flow shuttle valve.

In an even further embodiment according to the present invention, an apparatus for analyzing a sample of fluid using chromatography includes a first fluid path of effluent from a chromatography column or cartridge; at least one detector that is capable of analyzing the sample of fluid; and a shuttle valve that transfers an aliquot sample of fluid from the first fluid path to the detector(s) without substantially affecting the flow properties of fluid through the first fluid path. The flow of the fluid through the first fluid path may be substantially laminar, due to the first fluid path or channel being substantially linear or straight through at least a portion of the valve. In a further exemplary embodiment, the pressure of the fluid through the first fluid path remains substantially constant and/or it does not substantially increase. In another embodiment, the flow rate of the fluid may be substantially constant through the first fluid path. In an alternative embodiment, a second fluid path is utilized to carry the aliquot sample of fluid from the shuttle valve to the detector(s). The flow of fluid through the second fluid path may be substantially laminar due to the second fluid path or channel being substantially linear or straight through at least a portion of the valve. In an exemplary embodiment, the pressure of fluid through the second fluid path is substantially constant and/or it does not substantially increase. In further embodiment, the flow rate of fluid may be substantially constant through the second fluid path.

In an even further exemplary embodiment, an apparatus for analyzing a sample of fluid using chromatography includes a first fluid path of effluent from a chromatography column; a second fluid path that carries the sample of fluid to at least one detector that is capable of analyzing the sample; and a shuttle valve that transfers an aliquot sample of fluid from the first fluid path to the second fluid path while maintaining a continuous second fluid path through the shuttle valve. In one embodiment, a continuous first flow path through the shuttle valve is maintained when the aliquot sample of fluid is removed from the first fluid path. In another embodiment, continuous first and second flow paths through the shuttle valve are maintained when the aliquot sample of fluid is removed from the first fluid path and transferred to the second fluid path.

In a further exemplary embodiment, the apparatus for analyzing a sample comprises (i) a chromatography column; (ii) two or more non-destructive detectors with no destructive detectors within the system; (iii) a fraction collector in fluid communication with the two or more non-destructive detectors, the fraction collector being operatively adapted to collect one or more sample fractions in response to one or more detector signals from the two or more non-destructive detectors.

In an even further embodiment according to the present invention, an apparatus for analyzing a sample using flash chromatography includes an evaporative particle detector that is capable of detecting individual compounds in the sample; and a fraction collector that is capable of responding to a change in a detector response of the detected compound, wherein the evaporative particle detector is the only detector utilized to analyze the sample. The evaporative particle detector is capable of detecting chemical composition, chemical structure, molecular weight, or other physical or chemical properties. The detector may include an ELSD, CNLSD or mass spectrometer.

In yet another exemplary embodiment, the apparatus for analyzing a sample comprises a fraction collector in a liquid chromatography system, the fraction collector being operatively adapted to (i) recognize, receive and process one or more signals from at least one detector, and (ii) collect one or more sample fractions based on the one or more signals.

The methods and apparatus of the present invention may comprise at least one detector. Suitable detectors include, but are not limited to, non-destructive detectors (i.e., detectors that do not consume or destroy the sample during detection) such as UV, RI, conductivity, fluorescence, light scattering, viscometry, polorimetry, and the like; and/or destructive detectors (i.e., detectors that consume or destroy the sample during detection) such as evaporative particle detectors (EPD), e.g., evaporative light scattering detectors (ELSD), condensation nucleation light scattering detectors (CNLSD), ect., corona discharge, mass spectrometry, atomic adsorption, and the like. For example, the apparatus of the present invention may include at least one UV detector, at least one evaporative light scattering detector (ELSD), at least one mass spectrometer (MS), at least one condensation nucleation light scattering detector (CNLSD), at least one corona discharge detector, at least one refractive index detector (RID), at least one fluorescence detector (FD), chiral detector (CD) or any combination thereof. In one exemplary embodiment, the detector may comprise one or more evaporative particle detector(s) (EPD), which allows the use of chromaphoric and non-chromaphoric solvents as the mobile phase. In a further embodiment, a non-destructive detector may be combined with a destructive detector, which enables detection of various compound specific properties, molecular weight, chemical structure, elemental composition and chirality of the sample, such as, for example, the chemical entity associated with the peak.

The present invention is even further directed to computer readable medium having stored thereon computer-executable instructions for performing one or more of the method steps in any of the exemplary methods described herein. The computer readable medium may be used to load application code onto an apparatus or an apparatus component, such as any of the apparatus components described herein, in order to (i) provide interface with an operator and/or (ii) provide logic for performing one or more of the method steps described herein.

These and other features and advantages of the present invention will become apparent after a review of the following detailed description of the disclosed embodiments and the appended claims.

DETAILED DESCRIPTION OF THE INVENTION

Figure 1:
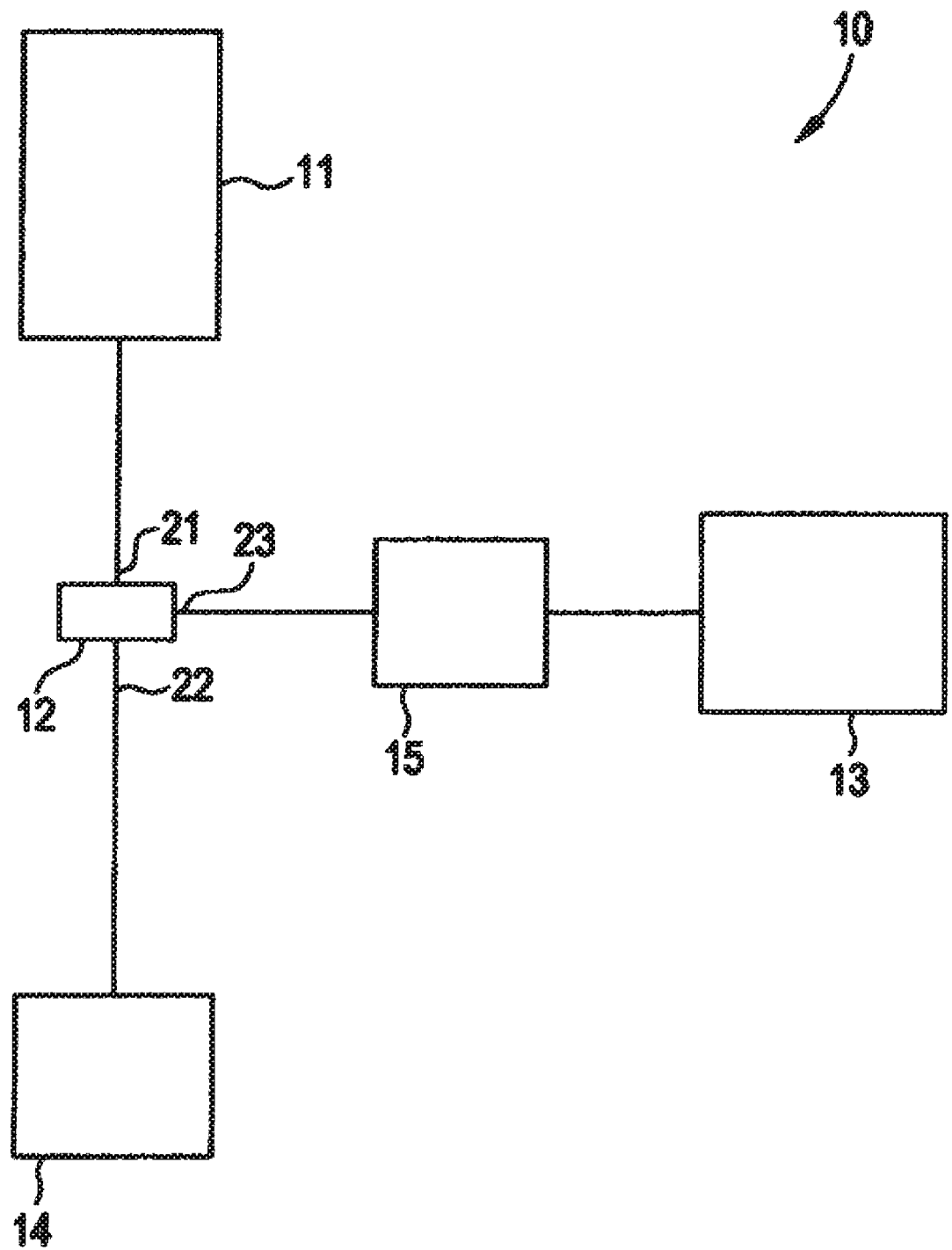
FIG. 1 depicts an exemplary liquid chromatography system of the present invention comprising a splitter pump to actively control fluid flow to a detector.

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

It must be noted that as used herein and in the appended claims, the singular forms "a", "and", and "the" include plural referents unless the context clearly dictates otherwise. Thus, for example, reference to "a solvent" includes a plurality of such solvents and reference to "solvent" includes reference to one or more solvents and equivalents thereof known to those skilled in the art, and so forth.

"About" modifying, for example, the quantity of an ingredient in a composition, concentrations, volumes, process temperatures, process times, recoveries or yields, flow rates, and like values, and ranges thereof, employed in describing the embodiments of the disclosure, refers to variation in the numerical quantity that may occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

As used herein, the term "chromatography" means a physical method of separation in which the components to be separated are distributed between two phases, one of which is stationary (stationary phase) while the other (the mobile phase) moves in a definite direction.

As used herein, the term "liquid chromatography" means the separation of mixtures by passing a fluid mixture dissolved in a "mobile phase" through a column comprising a stationary phase, which separates the analyte (i.e., the target substance) from other molecules in the mixture and allows it to be isolated.

As used herein, the term "mobile phase" means a fluid liquid, a gas, or a supercritical fluid that comprises the sample being separated and/or analyzed and the solvent that moves the sample comprising the analyte through the column. The mobile phase moves through the chromatography column or cartridge (i.e., the container housing the stationary phase) where the analyte in the sample interacts with the stationary phase and is separated from the sample.

As used herein, the term "stationary phase" means material fixed in the column or cartridge that selectively adsorbs the analyte from the sample in the mobile phase separation of mixtures by passing a fluid mixture dissolved in a "mobile phase" through a column comprising a stationary phase, which separates the analyte to be measured from other molecules in the mixture and allows it to be isolated.

As used herein, the term "flash chromatography" means the separation of mixtures by passing a fluid mixture dissolved in a "mobile phase" under pressure through a column comprising a stationary phase, which separates the analyte (i.e., the target substance) from other molecules in the mixture and allows it to be isolated.

As used herein, the term "shuttle valve" means a control valve that regulates the supply of fluid from one or more source(s) to another location. The shuttle valve may utilize rotary or linear motion to move a sample from on fluid to another.

As used herein, the term "fluid" means a gas, liquid, and supercritical fluid.

As used herein, the term "laminar flow" means smooth, orderly movement of a fluid, in which there is no turbulence, and any given subcurrent moves more or less in parallel with any other nearby subcurrent.

As used herein, the term "substantially" means within a reasonable amount, but includes amounts which vary from about 0% to about 50% of the absolute value, from about 0% to about 40%, from about 0% to about 30%, from about 0% to about 20% or from about 0% to about 10%.

The present invention is directed to methods of analyzing samples and collecting sample fractions. The present invention is further directed to apparatus capable of analyzing samples and collecting sample fractions. The present invention is even further directed to computer software suitable for use in an apparatus or apparatus component that is capable of analyzing samples and collecting sample fractions, wherein the computer software enables the apparatus to perform one or more method steps as described herein.

A description of exemplary methods of analyzing samples and apparatus capable of analyzing samples is provided below.

I. Methods of Analyzing Samples

The present invention is directed to methods of analyzing samples and collecting sample fractions. The methods of analyzing a sample may contain a number of process steps, some of which are described below.

A. Active Control of Fluid Flow to a Detector

In some embodiments of the present invention, the method of analyzing a sample comprises a step comprising actively controlling fluid flow to a detector via a splitter pump or a shuttle valve. One exemplary liquid chromatography system depicting such a method step is shown in FIG. 1. As shown in FIG. 1, exemplary liquid chromatography system 10 comprises (i) a chromatography column 11, (ii) a tee 12 having a first inlet 21, a first outlet 22 and a second outlet 23, (iii) a fraction collector 14 in fluid communication with first outlet 22 of tee 12, (iv) a first detector 13 in fluid communication with second outlet 23 of tee 12, and (v) a splitter pump 15 positioned in fluid communication with second outlet 23 of tee 12 and first detector 13.

In this exemplary system, splitter pump 15 actively controls fluid flow to first detector 13. As used herein, the phrase "actively controls" refers to the ability of a given splitter pump or shuttle valve to control fluid flow through a given detector even though there may be changes in fluid flow rate in other portions of the liquid chromatography system. Unlike "passive" flow splitters that merely split fluid flow, the splitter pumps and shuttle valves used in the present invention control fluid flow to at least one detector regardless of possible fluctuations in fluid flow within the liquid chromatography system such as, for example, flow restrictions, total flow rate, temperature, and/or solvent composition.

The step of actively controlling fluid flow to a given detector may comprise, for example, sending an activation signal to the splitter pump or shuttle valve to (i) activate the splitter pump or shuttle valve, (ii) deactivate the splitter pump or shuttle valve, (iii) change one or more flow and/or pressure settings of the splitter pump or shuttle valve, or (iv) any combination of (i) to (iii). Suitable flow and pressure settings include, but are not limited to, (i) a valve position, (ii) splitter pump or shuttle valve pressure, (iii) air pressure to a valve, or (iv) any combinations of (i) to (iii). Typically, the activation signal is in the form of, for example, an electrical signal, a pneumatic signal, a digital signal, or a wireless signal.

As shown in FIG. 1, in exemplary liquid chromatography system 10, the step of actively controlling fluid flow to detector 13 comprises using splitter pump 15 to pump fluid from tee 12 into detector 13. In other embodiments, the step of actively controlling fluid flow to a detector may comprise using a splitter pump to pull fluid through a detector. Such a system configuration is shown in FIG. 2.

Figure 2:
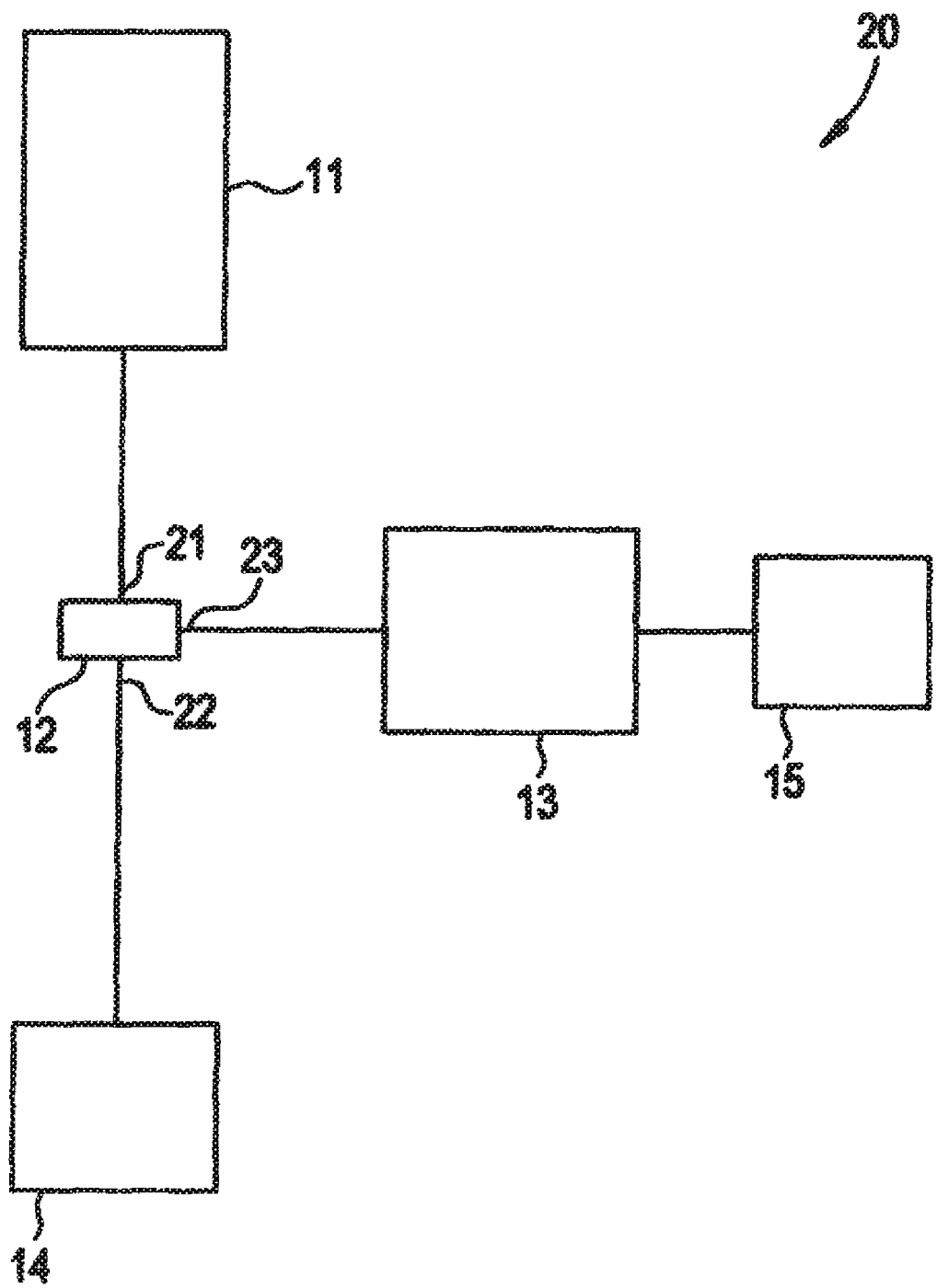
FIG. 2 depicts another exemplary liquid chromatography system of the present invention comprising a splitter pump and a detector.

FIG. 2 depicts exemplary liquid chromatography system 20 comprises chromatography column 11; tee 12 having first inlet 21, first outlet 22 and second outlet 23; fraction collector 14 in fluid communication with first outlet 22 of tee 12; first detector 13 in fluid communication with second outlet 23 of tee 12; and splitter pump 15 positioned so as to pull fluid through detector 13 from second outlet 23 of tee 12.

Figure 3A:
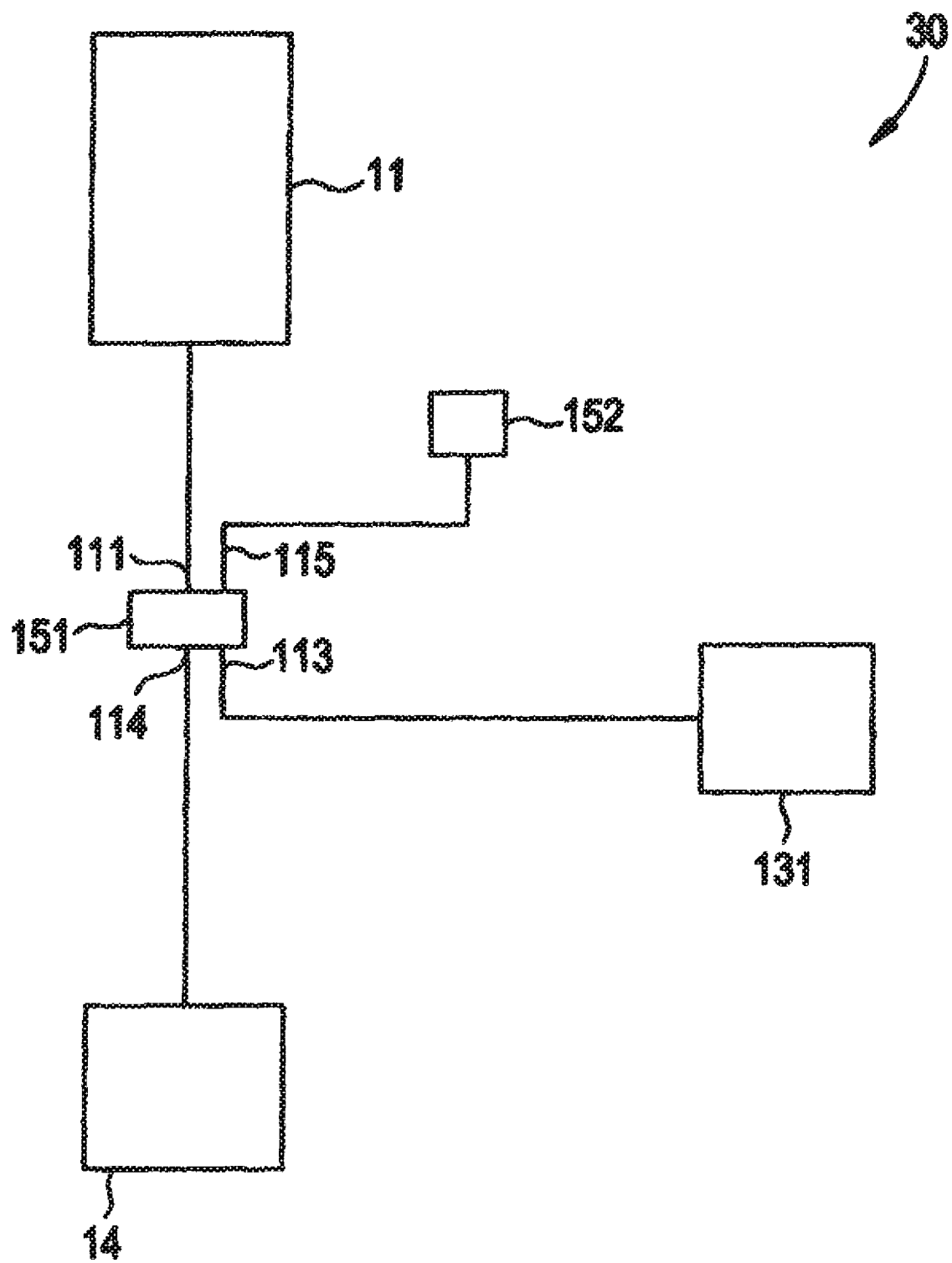
FIG. 3A depicts an exemplary liquid chromatography system of the present invention comprising a shuttle valve and a detector.
Figure 3B:
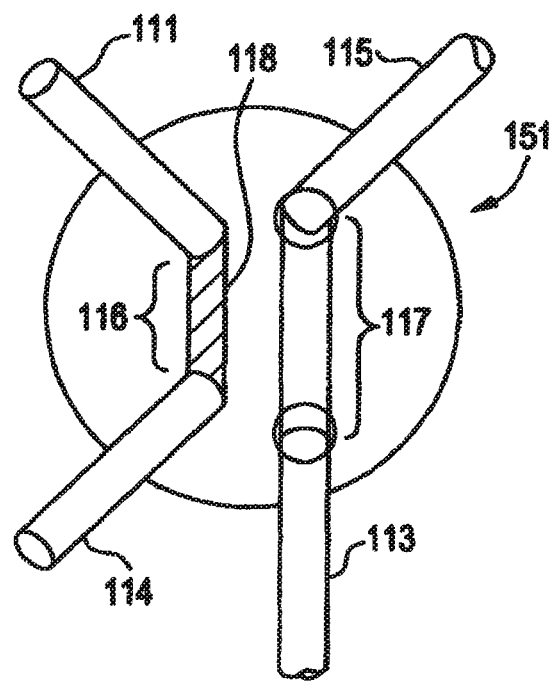
FIGS. 3B-3C depict the operation of an exemplary shuttle valve suitable for use in the present invention.
Figure 3C:
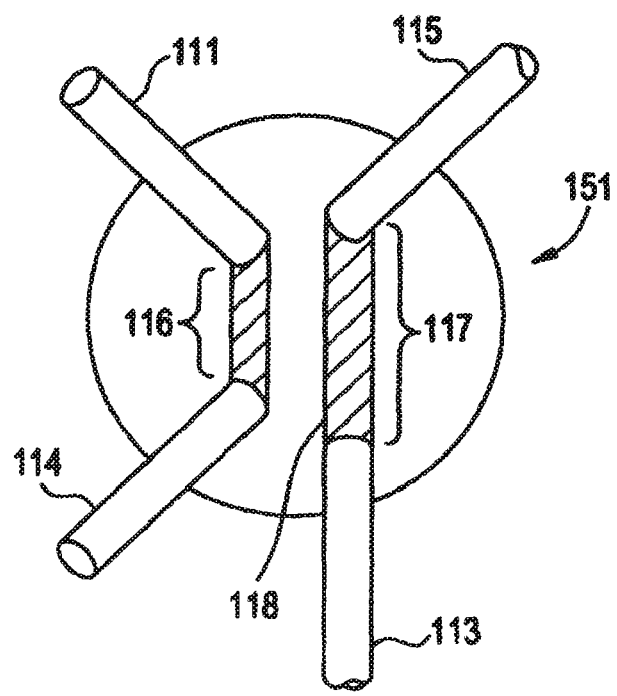

In some desired embodiments, a shuttle valve, such as exemplary shuttle valve 151 shown in FIGS. 3A-3C is used to actively control fluid flow to a detector such as detector 131. As shown in FIG. 3A, exemplary liquid chromatography system 30 comprises chromatography column 11; shuttle valve 151 having chromatography cartridge inlet 111, fraction collector outlet 114, gas or liquid inlet 115 and detector outlet 113; fraction collector 14 in fluid communication with fraction collector outlet 114 of shuttle valve 151; first detector 131 in fluid communication with detector outlet 113 of shuttle valve 151; and fluid supply 152 providing fluid to gas or liquid inlet 115 of shuttle valve 151.

In an even further exemplary embodiment of the present invention, a method of analyzing a sample of fluid using chromatography includes the steps of providing a first fluid of effluent from a chromatography column; providing a second fluid to carry the sample of fluid to at least one detector; using a shuttle valve to remove an aliquot sample of fluid from the first fluid and transfer the aliquot to the second fluid while maintaining a continuous path of the second fluid through the shuttle valve; using at least one detector to observe the aliquot sample of fluid; and collecting a new sample fraction of the first fluid in a fraction collector in response to a change in a detector response. In one embodiment, a continuous flow path of the first fluid through the shuttle valve is maintained when the aliquot sample of fluid is removed from the first fluid. In another embodiment, continuous flow paths of both the first fluid and the second fluid through the shuttle valve are maintained when the aliquot sample of fluid is removed from the first fluid and transferred to the second fluid.

In another exemplary embodiment according to the present invention, a method of analyzing a sample of fluid using chromatography includes the steps of providing a first fluid comprising the sample; using a shuttle valve to remove an aliquot sample of fluid from the first fluid without substantially affecting flow properties of the first fluid through the shuttle valve; using at least one detector to observe the aliquot sample of fluid; and collecting a new sample fraction of the first stream in a fraction collector in response to a change in at least one detector response. The flow of the first fluid through the shuttle valve may be substantially laminar, due to the first fluid path or channel being substantially linear or straight through at least a portion of the valve. In a further exemplary embodiment, the pressure of the first fluid through the shuttle valve remains substantially constant and/or it does not substantially increase. In another embodiment, the flow rate of the first fluid may be substantially constant through the shuttle valve. In an alternative embodiment, a second fluid is utilized to carry the aliquot sample of fluid from the shuttle valve to the detector(s). The flow of the second fluid through the shuttle valve may be substantially laminar due to the second fluid path or channel being substantially linear or straight through at least a portion of the valve. In an exemplary embodiment, the pressure of the second fluid through the shuttle valve is substantially constant and/or it does not substantially increase. In another embodiment, the flow rate of the second fluid may be substantially constant through the shuttle valve.

FIGS. 3B-3C depict how a shuttle valve in one exemplary embodiment operates within a given liquid chromatography system. As shown in FIG. 3B, shuttle valve 151 comprises chromatography cartridge inlet 111, which provides fluid flow from a chromatography column (e.g., column 11) to shuttle valve 151; an incoming sample aliquot volume 116; fraction collector outlet 114, which provides fluid flow from shuttle valve 151 to a fraction collection (e.g., fraction collection 14); gas or liquid inlet 115, which provides gas (e.g., air, nitrogen, etc.) or liquid (e.g., an alcohol) flow through a portion of shuttle valve 151; outgoing sample aliquot volume 117; and detector outlet 113, which provides fluid flow from shuttle valve 151 to a detector (e.g., detector 131, such as a ELSD).

As fluid flows through shuttle valve 151 from chromatography cartridge to inlet 111 to fraction collector outlet 114, incoming sample aliquot volume 116 is filled with a specific volume of fluid referred to herein as sample aliquot 118 (shown as the shaded area in FIG. 3B). At a desired time, shuttle valve 151 transfers sample aliquot 118 within incoming sample aliquot volume 116 into outgoing sample aliquot volume 117 as shown in FIG. 3C. Once sample aliquot 118 is transferred into outgoing sample aliquot volume 117, gas or liquid flowing from inlet 115 through outgoing sample aliquot volume 117 transports sample aliquot 118 to detector 131 (e.g., an ELSD) via detector outlet 113.

Shuttle valve 151 may be programmed to remove a sample aliquot (e.g., sample aliquot 118) from a sample for transport to at least one detector at a desired sampling frequency. In one exemplary embodiment, the sampling frequency is at least 1 sample aliquot every 10 seconds (or at least 1 sample aliquot every 5 seconds, or at least 1 sample aliquot every 3 seconds, or at least 1 sample aliquot every 2 seconds, or 1 sample aliquot every 0.5 seconds, or at least 1 sample aliquot every 0.1 seconds).

Figure 10A:
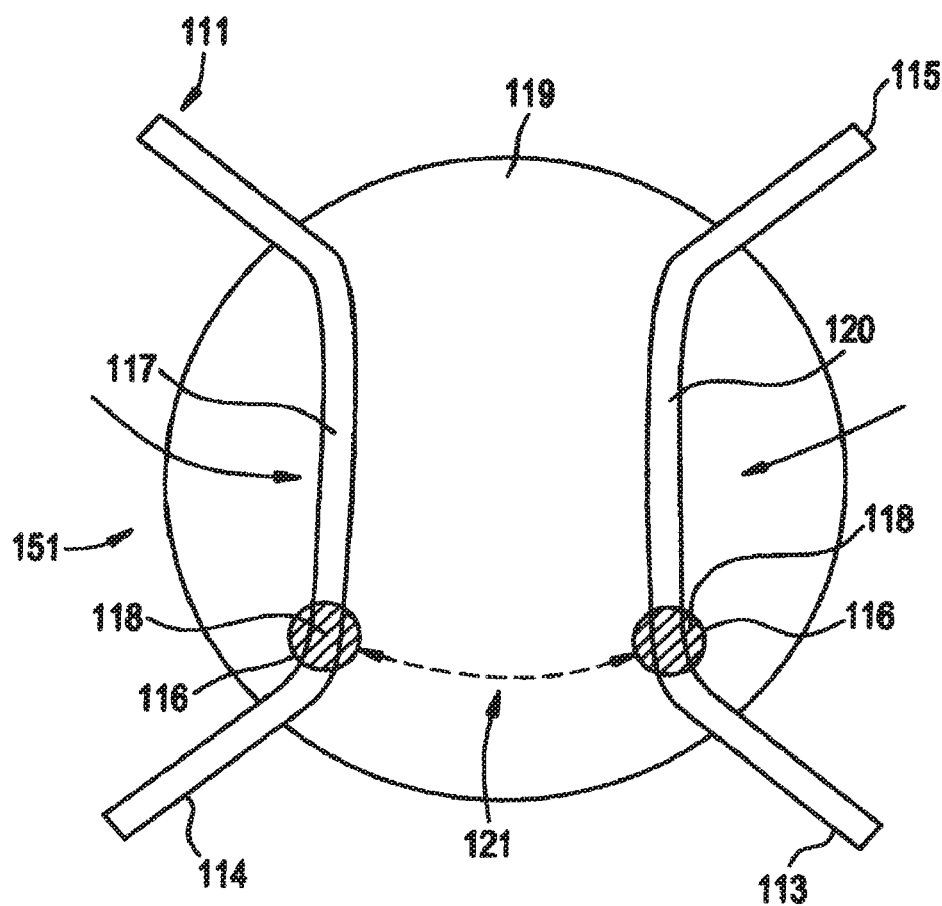
FIGS. 10A-10C depict the operation of an exemplary shuttle valve suitable for use in the present invention.
Figure 10B:
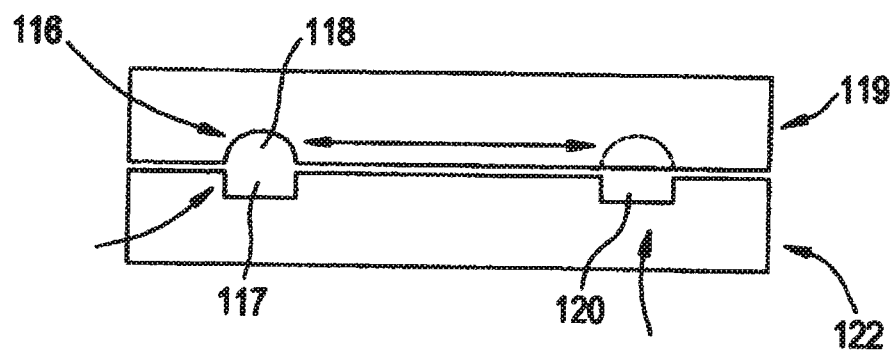
Figure 10C:
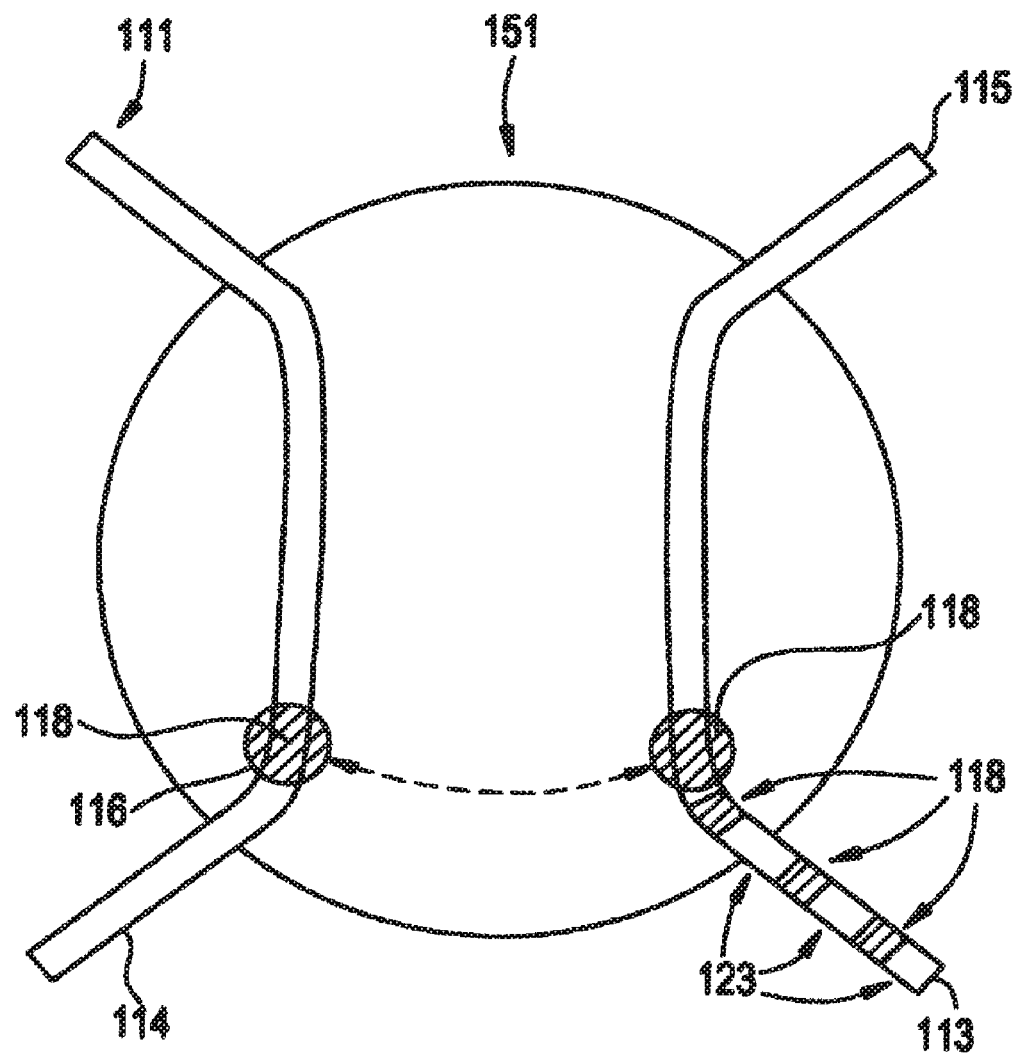

FIGS. 10A-C depict an exemplary shuttle valve of the present invention and how it operates within a given liquid chromatography system. As shown in FIG. 10A, shuttle valve 151 comprises chromatography cartridge inlet 111, which provides fluid flow from a chromatography column (e.g., column 11) to shuttle valve 151; channel 117 connecting inlet 111 to outlet 114; an incoming sample aliquot volume 118 in dimple 116 of dynamic body 119; fraction collector outlet 114, which provides fluid flow from shuttle valve 151 to a fraction collection (e.g., fraction collection 14); gas or liquid inlet 115, which provides gas (e.g., air, nitrogen, etc.) or liquid (e.g., an alcohol) flow through shuttle valve 151; outgoing sample aliquot volume 118 in dimple 116; channel 120 connecting inlet 115 to outlet 113; and detector outlet 113, which provides fluid flow from shuttle valve 151 to a detector (e.g., detector 131, such as a ELSD).

As fluid flows through shuttle valve 151 from chromatography cartridge to inlet 111 to fraction collector outlet 114 via channel 117, incoming sample aliquot volume 118 in dimple 116 is filled with a specific volume of fluid referred to herein as sample aliquot 118 (shown as the shaded area in FIG. 10A). At a desired time, shuttle valve 151 transfers sample aliquot 118 within dimple 116 taken from channel 117 to channel 120 by rotating the dimple 116 in dynamic body 119 via dimple rotation path 121. Once sample aliquot 118 is transferred into channel 120, gas or liquid flowing from inlet 115 through channel 120 transports sample aliquot 118 to detector 131 (e.g., an ELSD) via detector outlet 113. Another advantage of the shuttle valve of the present invention relates to the fluidics design of the channels through the valve. In order to minimize backpressure in the chromatography system, the flow through channels 117 and 120 is continuous. This is accomplished by locating channels 117 and 120 in static body 122 such that no matter what position the dynamic body 119 is in, the flow through shuttle valve 151 is continuous (as shown in FIG. 10B). As shown in FIG. 10A, at least a portion of the sample stream channel 117 and detector stream channel 120 may be substantially planar or circumferential, which reduces turbulence and further minimizes pressure increase through the valve. In addition, at least a portion of the sample stream channel 117 and detector stream channel 120 may be substantially parallel to dimple 116 when contiguous with it, which further limits turbulent flow and any increase in pressure in the valve. This includes those configurations that do not increase pressure within the valve of more than 50 psi, preferably not more than 30 psi, more preferably not more than 20 psi, and even more preferably not more than 10, 9, 8, 7, 6, 5, 4, 3, 2, or 1 psi. Dimple 116 is located in the dynamic body 119 and is in fluid communication with the face of the dynamic body that is contiguous with the static body 122, whereby when the dynamic body 119 is in a first position, the dimple 116 will be in fluid communication with the sample stream channel 117, and when moved to a second position, the dimple 116 will be in fluid communication with the detector stream channel 120. The dimple 116 may be of any shape but is depicted as a concave semi sphere, and it may be or any size. In an exemplary embodiment, the dimple may be extremely small in size (e.g., less than 2000 nL, preferably less than about 500 nL, more preferably less than about 100 nL, and even more preferably less than about 1 nL, but may include any size from 1 nL to 2000 nL, which allows for rapid sampling. In addition, small dimple 116 size allows for a very short dimple rotation path 121, which significantly reduces wear on the surfaces of the dynamic body 119 and the static body 122 and results in a shuttle valve 151 having extended service life before maintenance is required (e.g., more than 10 million cycles are possible before service). Even though a rotary motion shuttle valve is depicted in FIG. 10A-C, linear motion shuttle valves, or their equivalent, may be employed in the present invention.

Shuttle valve 151 may be programmed to remove a sample aliquot (e.g., sample aliquot 118) from a sample for transport to at least one detector at a desired sampling frequency. In one exemplary embodiment, the sampling frequency is at least 1 sample aliquot every 10 seconds (or at least 1 sample aliquot every 5 seconds, or at least 1 sample aliquot every 3 seconds, or at least 1 sample aliquot every 2 seconds, or 1 sample aliquot every 0.5 seconds, or at least 1 sample aliquot every 0.1 seconds). This shuttle valve is further described in copending U.S. provisional patent application No. 61/200,814, the entire subject matter of which is incorporated herein by reference.

In another embodiment, universal carrier fluid, including volatile liquids and various gases, may be utilized in the chromatography system to carry a sample to a detector. As shown in FIG. 3A, the carrier fluid from fluid supply 152 enters the shuttle valve 151 at inlet 115 where it picks up sample aliquot 118 (shown in FIG. 10A) and then proceeds via outlet 113 to detector 131. The sample aliquot should not precipitate in the carrier fluid of the valve or the associated plumbing may become blocked, or the sample will coat the walls of the flow path and some or all of the sample will not reach the detector. Sample composition in flash chromatography is very diverse, covering a large spectrum of chemical compounds including inorganic molecules, organic molecules, polymers, peptides, proteins, and oligonucleotides. Solubility in various solvents differs both within and between classes of compounds. Detector compatibility also constrains the types of carrier fluids that may be used. For example, for UV detection, the solvent should be non-chromaphoric at the detection wavelength. For evaporative particle detection (EPD) techniques (ELSD, CNLSD, Mass spec, etc.), the solvent should be easily evaporated at a temperature well below the sample's melting point. In addition, the carrier fluid should be miscible with the sample flowing between the valve inlet 111 and the fraction collector outlet 114. For example, if hexane is used in one flow path, water may not be used in the other flow path because the two are not miscible. All the above suggests the carrier fluid should be customized each time the separation solvents change. This is time consuming and impractical. According to an exemplary embodiment of the present invention, using solvents that are miscible with organic solvents and water, volatile, and non-chromaphoric, averts this problem. For example, a volatile, non-chromaphoric medium polarity solvent, such as isopropyl alcohol (IPA), may be used as the carrier fluid. IPA is miscible with almost all solvents, is non-chromaphoric at common UV detection wavelengths, and is easily evaporated at low temperatures. In addition, IPA dissolves a broad range of chemicals and chemical classes. IPA is thus a suitable carrier fluid for virtually all sample types. Other carrier fluids may include acetone, methanol, ethanol, propanol, butanol, isobutanol, tetrahydrofuran, and the like. In an alternative exemplary embodiment, a gas may be utilized as the carrier fluid. Sample precipitation is not encountered because the sample remains in the separation solvent, or mobile phase, through the shuttle valve and subsequently through the detector. Likewise, the separation solvent, or mobile phase, never mixes with another solvent so miscibility is not an issue. Because the carrier is a gas, volatility is no longer an issue. In addition, most gasses are non-chromaphoric and compatible with UV detection. When using gas as the carrier, the sample aliquot 118 is issued from the valve 151 to the detector 131 as discrete slugs sandwiched between gas pockets 123 as shown in FIG. 10C. Using gas as the carrier fluid has other advantages. For example, when used with an evaporative light scattering detector or other detection technique where the sample is nebulized, the gas may be used to transport the sample and nebulize the sample, eliminating the need for a separate nebulizer gas supply. In addition, because gas does not require evaporation, ambient drift tube temperatures may be used eliminating the need for drift tube heaters. A broader range of samples may be detected because those that would evaporate at higher temperatures will now stay in the solid or liquid state as they pass through the drift tube. A variety of gasses may be used as the carrier gas including air, nitrogen, helium, hydrogen and carbon dioxide. Supercritical fluids may also be used, such as supercritical carbon dioxide.

B. Detection of a Sample Component within a Fluid Stream

The methods of the present invention may further comprise using at least one detector to detect one or more sample components within a fluid stream. Suitable detectors for use in the liquid chromatography systems of the present invention include, but are not limited to, non-destructive and/or destructive detectors. Suitable detectors include, but are not limited to, non-destructive detectors (i.e., detectors that do not consume or destroy the sample during detection) such as UV, RI, conductivity, fluorescence, light scattering, viscometry, polorimetry, and the like; and/or destructive detectors (i.e., detectors that consume or destroy the sample during detection) such as evaporative particle detectors (EPD), e.g., evaporative light scattering detectors (ELSD), condensation nucleation light scattering detectors (CNLSD), etc., corona discharge, mass spectrometry, atomic adsorption, and the like. For example, the apparatus of the present invention may include at least one UV detector, at least one evaporative light scattering detector (ELSD), at least one mass spectrometer (MS), at least one condensation nucleation light scattering detector (CNLSD), at least one corona discharge detector, at least one refractive index detector (RID), at least one fluorescence detector (FD), at least one chiral detector (CD), or any combination thereof. In one exemplary embodiment, the detector may comprise one or more evaporative particle detector(s) (EPD), which allows the use of chromaphoric and non-chromaphoric solvents as the mobile phase. In a further embodiment, a non-destructive detector may be combined with a destructive detector, which enables detection of various compound specific properties of the sample, such as, for example, the chemical entity, chemical structure, molecular weight, etc., associated with each chromatographic peak. When combined with mass spectrometer detection, the fraction's chemical structure and/or molecular weight may be determined at the time of detection, streamlining identification of the desired fraction. In current systems the fraction's chemical identity and structure must be determined by cumbersome past-separation techniques.

Regardless of the type of detector used, a given detector provides one or more detector responses that may be used to generate and send a signal to one or more components (e.g., a fraction collector, another detector, a splitter pump, a shuttle valve, or a tee) within a liquid chromatography system as described herein. Typically, a change in a given detector response triggers the generation and sending of a signal. In the present invention, a change in a given detector response that might trigger the generation and sending of a signal to one or more components includes, but is not limited to, a change in a detector response value, reaching or exceeding a threshold detector response value, a slope of the detector response value over time, a threshold slope of the detector response value over time, a change in a slope of the detector response value over time, a threshold change in a slope of the detector response value over time, or any combination thereof.

Figure 4:
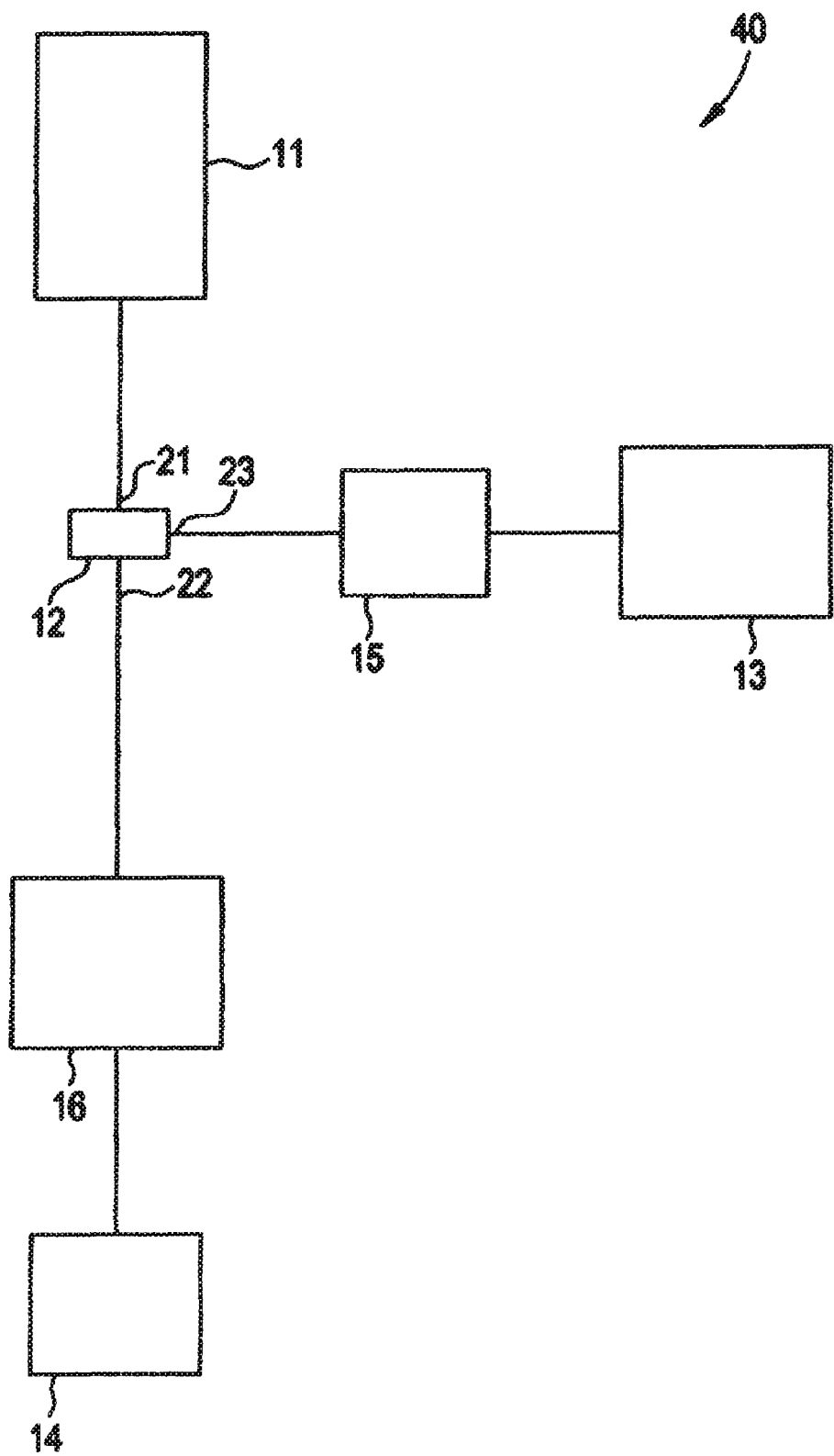
FIG. 4 depicts an exemplary liquid chromatography system of the present invention comprising a splitter pump and two detectors.

In some exemplary embodiments, the liquid chromatography system of the present invention comprises at least two detectors as shown in FIG. 4. Exemplary liquid chromatography system 40 shown in FIG. 4 comprises chromatography column 11; tee 12 having first inlet 21, first outlet 22 and second outlet 23; fraction collector 14 in fluid communication with first outlet 22 of tee 12; first detector 13 in fluid communication with second outlet 23 of tee 12; splitter pump 15 actively controlling fluid flow to first detector 13 from second outlet 23 of tee 12; and second detector 16 in fluid communication with second outlet 23 of tee 12.

When two or more detectors are present, the liquid chromatography system provides more analysis options to an operator. For example, in exemplary liquid chromatography system 40 shown in FIG. 4, a method of analyzing a sample may comprise a step of sending one or more signals from first detector 13 (e.g., an ELSD) and/or second detector 16 (e.g., an optical absorbance detector such as an UV detector) to fraction collector 14 instructing fraction collector 14 to collect a new sample fraction. The one or more signals from first detector 13 and/or second detector 16 may comprise a single signal from first detector 13 or second detector 16, two or more signals from first detector 13 and second detector 16, or a composite signal from first detector 13 and second detector 16. In exemplary liquid chromatography system 40 shown in FIG. 4, the method of analyzing a sample may further comprise a step of sending a signal from second detector 16 to splitter pump 15 instructing splitter pump 15 to initiate or stop fluid flow to first detector 13 in response to second detector 16 detecting a sample component in a fluid stream.

Figure 5:
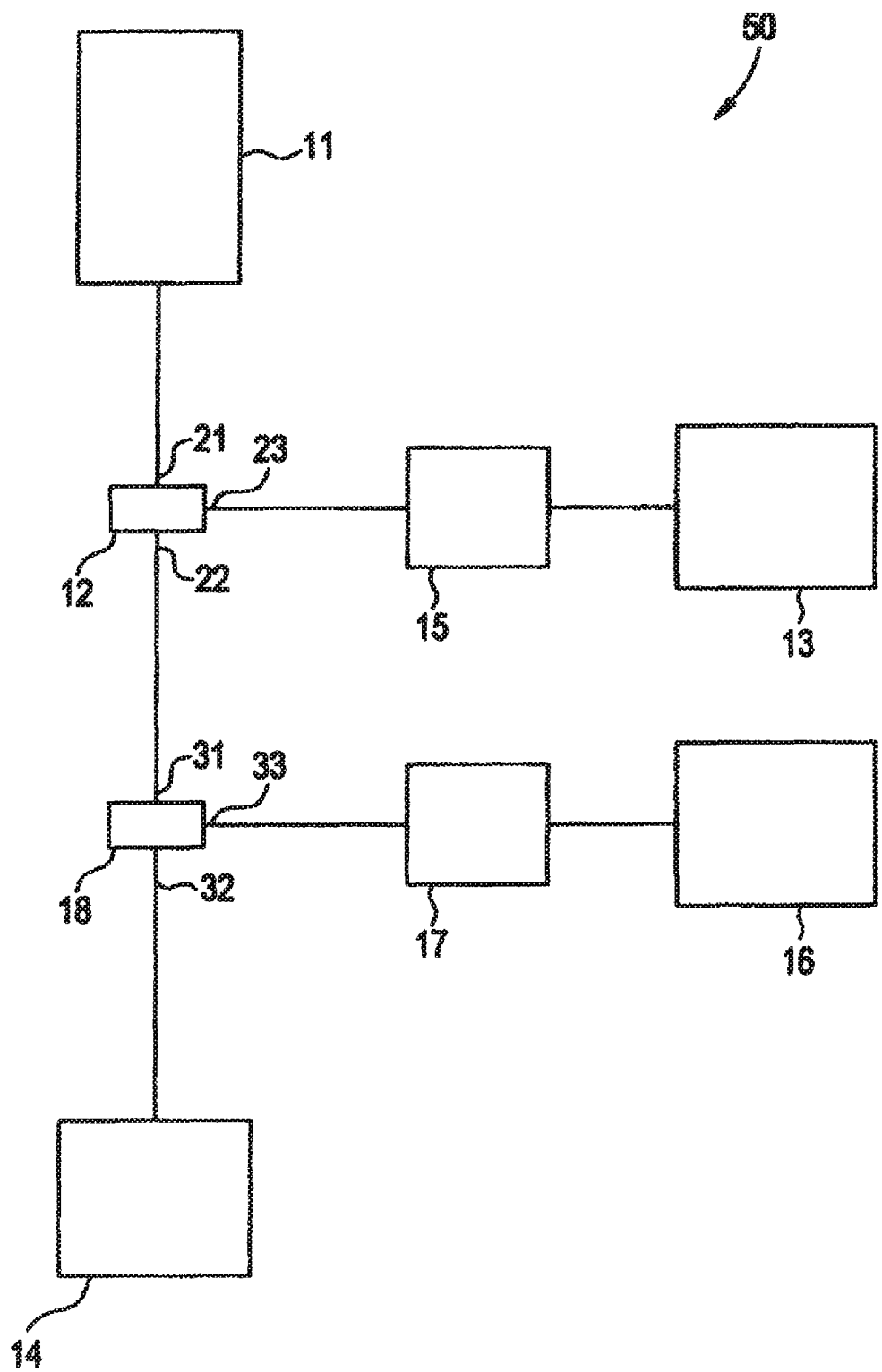
FIG. 5 depicts an exemplary liquid chromatography system of the present invention comprising two splitter pumps and two detectors.

In other exemplary embodiments, the liquid chromatography system of the present invention comprises at least two detectors and at least two splitter pumps as shown in FIG. 5. Exemplary liquid chromatography system 50 shown in FIG. 5 comprises chromatography column 11; first tee 12 having first inlet 21, first outlet 22 and second outlet 23; first detector 13 in fluid communication with second outlet 23 of first tee 12; first splitter pump 15 actively controlling fluid flow to first detector 13 from second outlet 23 of first tee 12; second tee 18 having first inlet 31, first outlet 32 and second outlet 33; second detector 16 in fluid communication with second outlet 33 of second tee 18; second splitter pump 17 actively controlling fluid flow to second detector 16 from second outlet 33 of second tee 18; and fraction collector 14 in fluid communication with second outlet 32 of second tee 18.

Figure 6:
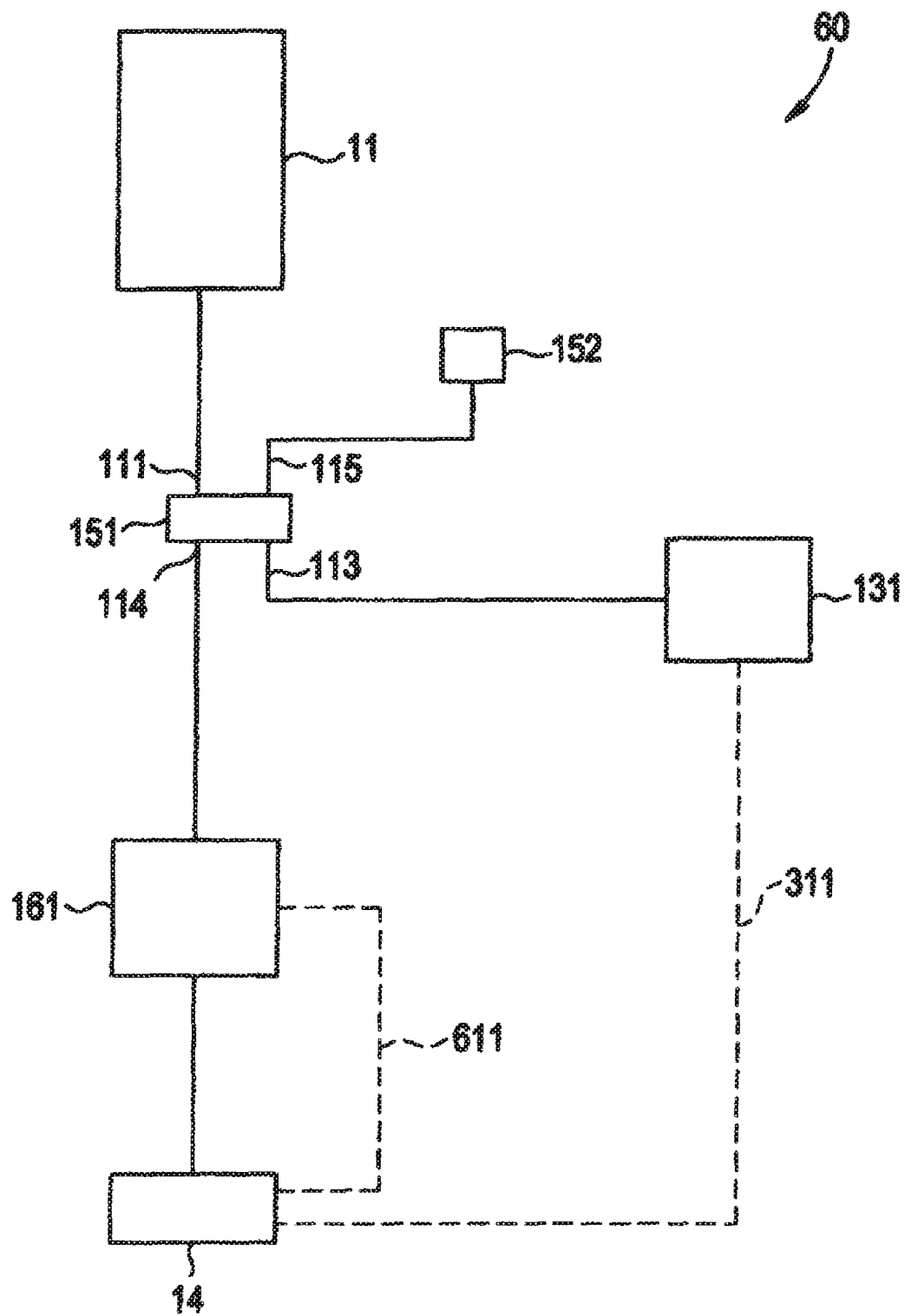
FIG. 6 depicts an exemplary liquid chromatography system of the present invention comprising a shuttle valve and two detectors.
Figure 7:
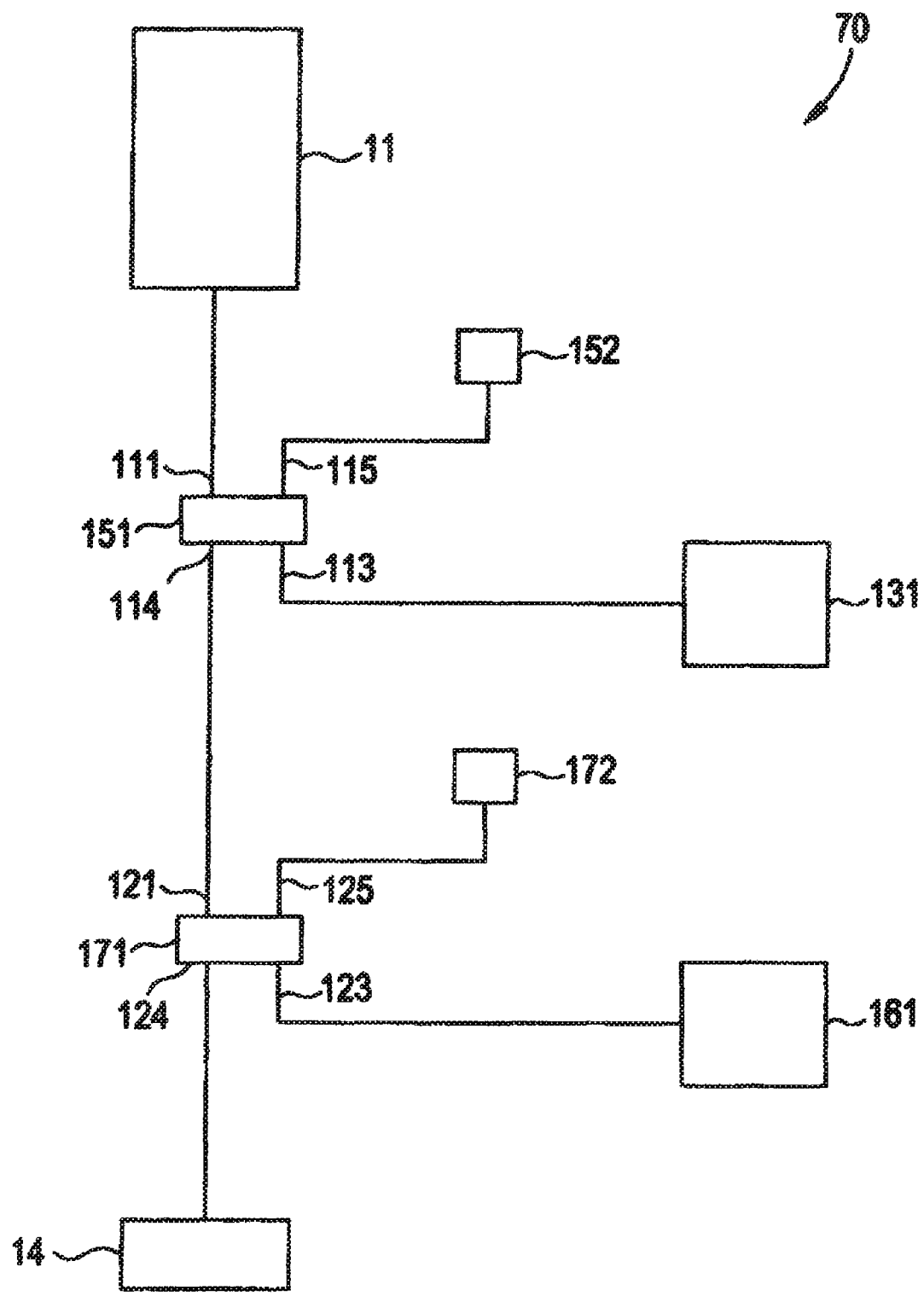
FIG. 7 depicts an exemplary liquid chromatography system of the present invention comprising two shuttle valves and two detectors.

As discussed above, the liquid chromatography systems of the present invention may comprise one or more shuttle valves in place or one or more tee/splitter pump combinations to actively control fluid flow to at least one detector as exemplified in FIGS. 6-7. As shown in FIG. 6, exemplary liquid chromatography system 60 comprises chromatography column 11; shuttle valve 151 having chromatography cartridge inlet 111, fraction collector outlet 114, gas or liquid inlet 115 and detector outlet 113; fraction collector 14 in fluid communication with fraction collector outlet 114 of shuttle valve 151; first detector 131 in fluid communication with detector outlet 113 of shuttle valve 151; fluid supply 152 providing fluid to gas or liquid inlet 115 of shuttle valve 151; and second detector 161 in fluid communication with detector outlet 113 of shuttle valve 151.

As shown in FIG. 7, exemplary liquid chromatography system 70 comprises chromatography column 11; first shuttle valve 151 having chromatography cartridge inlet 111, fraction collector outlet 114, gas or liquid inlet 115 and detector outlet 113; first detector 131 in fluid communication with detector outlet 113 of shuttle valve 151; fluid supply 152 providing fluid to gas or liquid inlet 115 of shuttle valve 151; second shuttle valve 171 having chromatography cartridge inlet 121, fraction collector outlet 124, gas or liquid inlet 125 and detector outlet 123; second detector 161 in fluid communication with detector outlet 123 of shuttle valve 171; fluid supply 172 providing fluid to gas or liquid inlet 125 of shuttle valve 171; and fraction collector 14 in fluid communication with fraction collector outlet 124 of shuttle valve 171.

In these exemplary embodiments, namely, exemplary liquid chromatography systems 50 and 70, a method of analyzing a sample may further comprise a step of actively controlling fluid flow to second detector 16 (or second detector 161) via second splitter pump 17 (or second shuttle valve 171), as well as actively controlling fluid flow to first detector 13 (or first detector 131) via first splitter pump 15 (or first shuttle valve 151). Although not shown in FIG. 5, it should be understood that first splitter pump 15 and/or second splitter pump 17 may be positioned within exemplary liquid chromatography system 50 so as to push or pull fluid through first detector 13 and second detector 16 respectively.

In some exemplary embodiments, one or more optical absorbance detectors, such as one or more UV detectors, may be used to observe detector responses and changes in detector responses at one or more wavelengths across the absorbance spectrum. In these embodiments, one or more light sources may be used in combination with multiple sensors within a single detector or multiple detectors to detect light absorbance by a sample at multiple wavelengths. For example, one or more UV detectors may be used to observe detector responses and changes in detector responses at one or more wavelengths across the entire UV absorbance spectrum.

In one exemplary method of analyzing a sample, the method comprises the step of using an optical absorbance detector, such as an UV detector, comprising n sensors to observe a sample at n specific wavelengths across the entire UV absorbance spectrum; and collecting a new sample fraction in response to (i) a change in any one of the n detector responses at the n specific UV wavelengths, or (ii) a change in a composite response represented by the n detector responses. The n sensors and multiple detectors, when present, may be positioned relative to one another as desired to affect signal timing to a fraction collector and/or another system component (e.g., another UV detector).

When utilizing whole-spectrum UV (or other spectrum range) analysis, the spectrum may be divided into any desired number of ranges of interest (e.g., every 5 nm range from 200 nm to 400 nm). Any significant change over time in each spectrum range may be monitored. A sudden drop in received light energy (e.g., a drop in both the first and second derivative of the detector response) within a given range may indicate the arrival of a substance that absorbs light in the given wavelength range of interest. In this exemplary embodiment, the width of each range can be made smaller to increase precision; alternatively, the width of each range can be made larger so as to reduce the burden of calculation (i.e., fewer calculations per second, less memory required).

Figure 8:
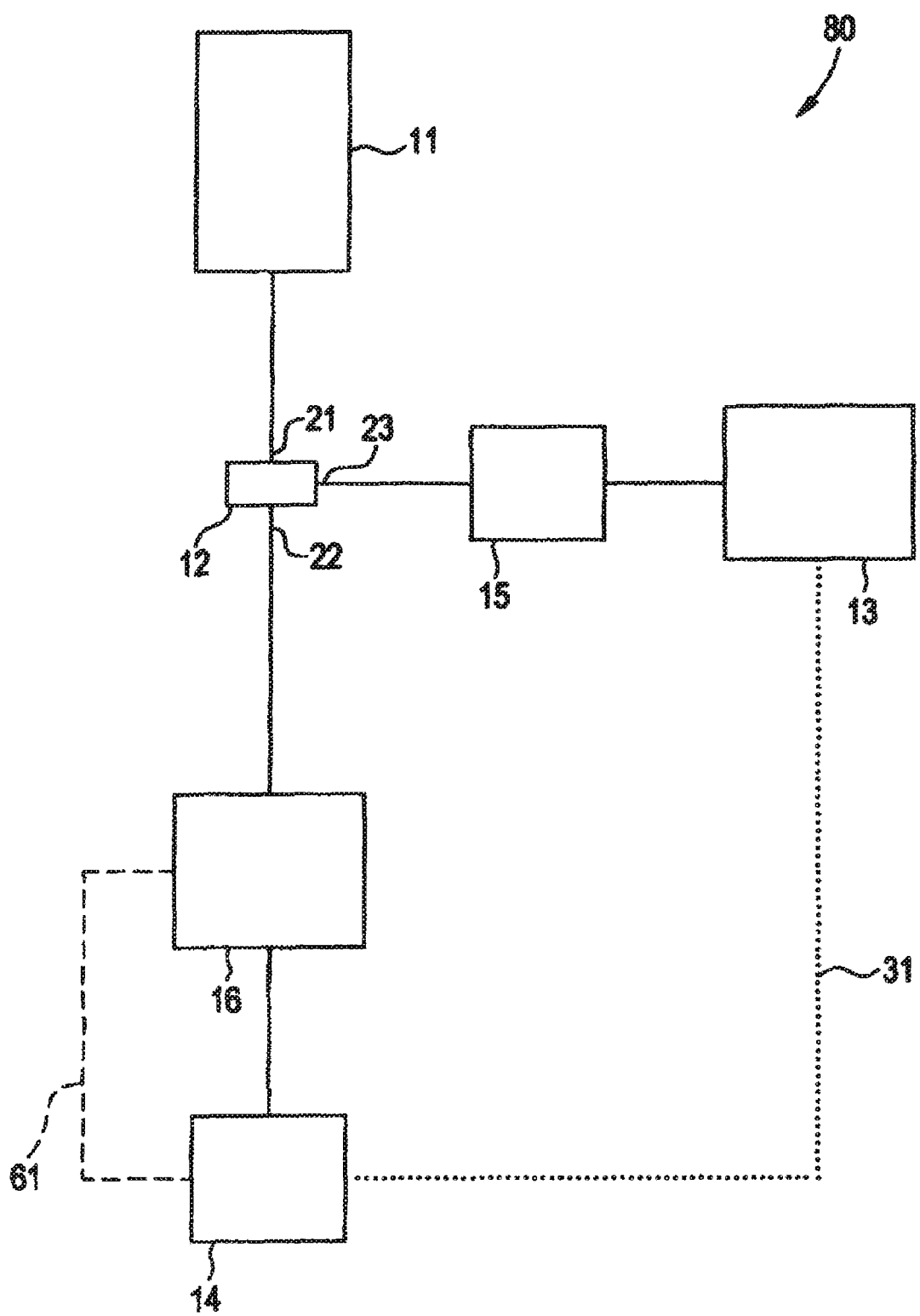
FIG. 8 depicts an exemplary liquid chromatography system of the present invention comprising a splitter pump, an evaporative light scattering detector (ELSD), and an ultraviolet (UV) detector.

In other exemplary embodiments, a plurality of different types of detectors may be used to observe a variety of detector responses and changes in the detector responses within a given system. In exemplary liquid chromatography system 80 shown in FIG. 8, an evaporative particle detector (EPD), such as an evaporative light scattering detector (ELSD) (i.e., first detector 13) is used alone or in combination with an UV detector (i.e., second detector 16). Exemplary liquid chromatography system 80 further comprises chromatography column 11; tee 12 having first inlet 21, first outlet 22 and second outlet 23; fraction collector 14; EPD 13 in fluid communication with second outlet 23 of tee 12; splitter pump 15 actively controlling fluid flow to EPD 13; and UV detector 16 in fluid communication with first outlet 22 of tee 12. In this exemplary embodiment, the use of evaporative particle detection offers several advantages. Non-chromaphoric mobile phases must be used with UV detection or the mobile phase's background absorbance would obliterate the sample signal. This precludes using solvents such as toluene, pyridine and others that have otherwise valuable chromatographic properties. With evaporative particle detection, the mobile phase chromaphoric properties are immaterial. As long as the mobile phase is more volatile than the sample, it may be used with evaporative particle detection. This opens the opportunity to improve separations through the use of highly selective chromaphoric solvents as the mobile phase. Moreover, UV detectors will not detect non-chromaphoric sample components. Fractions collected based on UV detection only may contain one or more unidentifiable non-chromaphoric components, which compromises fraction purity. Conversely, non-chromaphoric samples may be completely missed by UV detection and either sent directly to waste or collected in fractions assumed to be sample-free (blank fractions). The net result is lost productivity, contaminated fractions, or loss of valuable sample components. When an EPD (e.g., ELSD) is utilized alone or with UV detection in the flash system, chromaphoric and non-chromaphoric components are detected and collected, improving fraction purity. Because a flash system that includes UV detector alone may miss sample components or incorrectly flag pure fractions, many flash users will screen collected fractions by thin layer chromatography to confirm purity and confirm blank fractions are truly blank. This is a time-consuming post-separation procedure that slows down workflow. Those fractions discovered to contain more than one component will frequently require a second chromatography step to properly segregate the components.

In exemplary liquid chromatography system 80, signals 31 and 61 from detector (e.g., ELSD) 13 and UV detector 16 respectively may be sent to fraction collector 14 to initiate some activity from fraction collector 14 such as, for example, collection of a new sample fraction. In desired embodiments, in response to one or more detector signals 31 and 61 from (i) detector ELSD 13, (ii) UV detector 16, or (iii) both ELSD 13 and UV detector 16, fraction collector 14 collects a new sample fraction.

Similar to exemplary liquid chromatography system 80, in exemplary liquid chromatography system 60 shown in FIG. 6, signals 311 and 611 from ELSD 131 and UV detector 161 respectively may be sent to fraction collector 14 to initiate some activity from fraction collector 14 such as, for example, collection of a new sample fraction. In desired embodiments, in response to one or more detector signals 311 and 611 from (i) ELSD 131, (ii) UV detector 161, or (iii) both ELSD 131 and UV detector 161, fraction collector 14 collects a new sample fraction.

As discussed above, UV detector 16 (or UV detector 161) may comprise n sensors operatively adapted to observe a sample at n specific wavelengths across a portion of or the entire UV absorbance spectrum. In exemplary liquid chromatography system 80 shown in FIG. 8, in response to (i) a single signal from either one of ELSD 13 or UV detector 16, (ii) two or more signals from both ELSD 13 and UV detector 16, or (iii) a composite signal comprising two or more detector responses (i.e., up to n detector responses) at the two or more specific UV wavelengths (i.e., up to n specific UV wavelengths), fraction collector 14 collects a new sample fraction. Similarly, in exemplary liquid chromatography system 60 shown in FIG. 6, in response to (i) a single signal from either one of ELSD 131 or UV detector 161, (ii) two or more signals from both ELSD 131 and UV detector 161, or (iii) a composite signal comprising two or more detector responses (i.e., up to n detector responses) at the two or more specific UV wavelengths (i.e., up to n specific UV wavelengths), fraction collector 14 collects a new sample fraction.

Further, in exemplary liquid chromatography system 80, UV detector 16 may be used to produce a detector signal (not shown) that (1) results (i) from a single detector response from a single sensor or (ii) from n detector responses of n sensors with n being greater than 1, and (2) is sent to at least one of splitter pump 15, ELSD 13 and tee 12. In addition, a detector signal (not shown) resulting from a detector response in ELSD 13 may be sent to UV detector 16 to change one or more settings of UV detector 16. Similarly, in exemplary liquid chromatography system 60 shown in FIG. 6, UV detector 161 may be used to produce a detector signal (not shown) that (1) results (i) from a single detector response from a single sensor or (ii) from n detector responses of n sensors with n being greater than 1, and (2) is sent to at least one of shuttle valve 151 and ELSD 13. In addition, a detector signal (not shown) resulting from a detector response in ELSD 131 may be sent to UV detector 161 to change one or more settings of UV detector 161.

Figure 9:
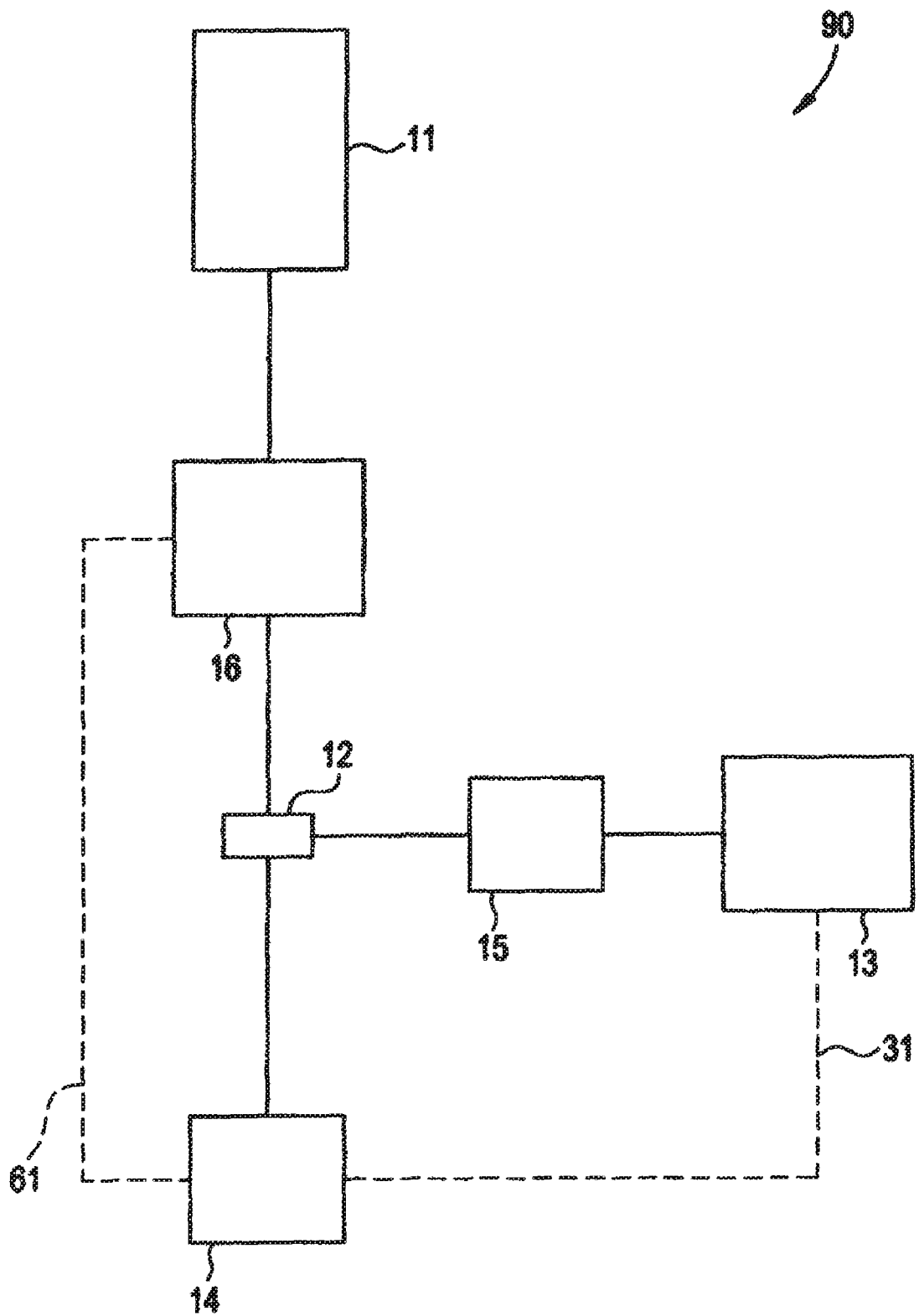
FIG. 9 depicts another exemplary liquid chromatography system of the present invention comprising a splitter pump, an ELSD and an UV detector.

As shown in exemplary liquid chromatography system 90 shown in FIG. 9, the position of different types of detectors within a given system may be adjusted as desired to provide one or more system process features. In exemplary liquid chromatography system 90, ELSD 13 is positioned downstream from UV detector 16. In such a configuration, UV detector 16 is positioned to be able to provide a detector response and generate signal 61 (e.g., a signal that results (i) from a single detector response from a single sensor or (ii) from n detector responses of n sensors with n being greater than 1) for fraction collector 14 prior to the generation of signal 31 from ELSD 13. UV detector 16 is also positioned to be able to provide a detector response and generate a signal (not shown) (e.g., a signal that results (i) from a single detector response from a single sensor or (ii) from n detector responses of n sensors with n being greater than 1) for at least one of splitter pump 15, ELSD 13 and tee 12 so as to activate or deactivate splitter pump 15, ELSD 13 and/or tee 12.

Although not shown, it should be understood that a shuttle valve may be used in place of tee 12 and splitter pump 15 within exemplary liquid chromatography system 90 shown in FIG. 9 to provide similar system process features. In such a configuration, UV detector 16 is positioned to be able to provide a detector response and generate signal 61 (e.g., a signal that results (i) from a single detector response from a single sensor or (ii) from n detector responses of n sensors with n being greater than 1) for fraction collector 14 prior to the generation of signal 31 from ELSD 13. UV detector 16 is also positioned to be able to provide a detector response and generate a signal (not shown) (e.g., a signal that results (i) from a single detector response from a single sensor or (ii) from n detector responses of n sensors with n being greater than 1) for at least one of a shuttle valve and ELSD 13 so as to activate or deactivate the shuttle valve and/or ELSD 13. Even though systems 60, 80, and 90 refer to ELSD and UV as the detectors, any destructive detector, such as EPD, may be utilized for the ELSD, and any nondestructive detector may be utilized in place of the UV detector.

In other exemplary embodiments, the liquid chromatography system of the present invention may comprise a non-destructive system comprising two or more non-destructive detectors (e.g., one or more optical absorbance detectors, such as the UV detectors described above) with no destructive detectors (e.g., a mass spectrometer) present in the system. In one exemplary embodiment, the liquid chromatography system comprises two optical absorbance detectors such as UV detectors, and the method of analyzing a sample comprises the step of using two or more detectors to observe a sample at two or more specific wavelengths; and collecting a new sample fraction in response to (i) a change in a first detector response at a first wavelength, (ii) a change in a second detector response at a second wavelength, or (iii) a change in a composite response represented by the first detector response and the second detector response. In these embodiments, the first wavelength may be substantially equal to or different from the second wavelength.

In embodiments utilizing two or more optical absorbance detectors, such as two or more UV detectors, the optical absorbance detectors may be positioned within a given liquid chromatography system so as to provide one or more system advantages. The two or more optical absorbance detectors may be positioned in a parallel relationship with one another so that a sample reaches each detector at substantially the same time, and the two or more optical absorbance detectors may produce and send signals (i.e., from first detector and second detector responses) at substantially the same time to a fraction collector.

In a further embodiment, a non-destructive detector (e.g., RI detector, UV detector, etc.) may be used alone or in combined with a destructive detector (e.g., EPD, mass spectrometer, spectrophotometer, emission spectroscopy, NMR, etc.). For example, a destructive detector, such as a mass spectrometer detector, enables simultaneous detection of the component peak and chemical entity associated with the peak. This allows for immediate determination of the fraction that contains the target compound. With the other detection techniques, post separation determination of which fraction contains the target compound may be required, such as by, for example, spectrophotometry, mass spectrometry, emission spectroscopy, NMR, etc. If two or more chemical entities elute at the same time from the flash cartridge (i.e., have the same retention time), they will be deposited in the same vial by the system when using certain detectors (i.e., those detectors that cannot identify differences between the chemical entities) because these detectors cannot determine chemical composition. In an exemplary embodiment where a mass spectrometer detector is utilized as the destructive detector, all compounds that elute at the same time may be identified. This eliminates the need to confirm purity after separation.

In any of the above-described liquid chromatography systems, it may be advantageous to position at least one detector, such as at least one UV detector, downstream from (e.g., in series with) at least one other detector, such as at least one other UV detector or an ELSD. In such an embodiment, a first detector response in a first detector can be used to produce and send a signal to at least one of (1) a splitter pump, (2) a shuttle valve, (3) a second detector and (4) a tee. For example, a first detector response in a first detector can be used to produce and send a signal to a splitter pump or a shuttle valve to (i) activate the splitter pump or the shuttle valve, (ii) deactivate the splitter pump or the shuttle valve, (iii) change one or more flow or pressure settings of the splitter pump or the shuttle valve, or (iv) any combination of (i) to (iii). Suitable flow and pressure settings include, but are not limited to, the flow and pressure settings described above. Typically, the signal is in the form of, for example, an electrical signal, a pneumatic signal, a digital signal, or a wireless signal.

In some embodiments, multiple detectors (i.e., two or more detectors) may be positioned so that each detector can send a signal to at least one of (1) a splitter pump, (2) a shuttle valve, (3) another detector and (4) a tee independently of the other detectors in the system. For example, multiple optical absorbance detectors (e.g., UV detectors) may be positioned within a given system to provide independent signals to a shuttle valve to cause the shuttle valve to provide actively controlled fluid sampling to another detector such as an ELSD.

In other embodiments, a first detector response in a first detector can be used to produce and send a signal to a second detector to (i) activate the second detector, (ii) activate the second detector at a wavelength substantially similar to a first wavelength used in the first detector, (iii) activate the second detector at a wavelength other than the first wavelength used in the first detector, (iv) deactivate the second detector, (v) change some other setting of the second detector (e.g., the observed wavelength of the second detector), or (vi) any combination of (i) to (v).

In yet other embodiments, a first detector response in a first detector can be used to produce and send a signal to a tee to (i) open a valve or (ii) close a valve so as to start or stop fluid flow through a portion of the liquid chromatography system. As discussed above, typically, the signal is in the form of, for example, an electrical signal, a pneumatic signal, a digital signal, or a wireless signal.

C. Generation of a Signal from a Detector Response

The methods of the present invention may further comprise the step of generating a signal from one or more detector responses. In some embodiments, such as exemplary liquid chromatography system 10 shown in FIG. 1, a single detector detects the presence of a sample component and produces a detector response based on the presence and concentration of a sample component within a fluid stream. In other embodiments, such as exemplary liquid chromatography system 50 shown in FIG. 6, two or more detectors may be used to detect the presence of one or more sample components, and produce two or more detector responses based on the presence and concentration of one or more sample components within a fluid stream.

As discussed above, a given detector provides one or more detector responses that may be used to generate and send a signal to one or more components (e.g., a fraction collector, another detector, a splitter pump, a shuttle valve, or a tee) within a liquid chromatography system as described herein. Typically, a change in a given detector response triggers the generation and sending of a signal. Changes in a given detector response that might trigger the generation and sending of a signal to one or more components include, but are not limited to, a change in a detector response value, reaching or exceeding a threshold detector response value, a slope of the detector response value over time, a threshold slope of the detector response value over time, a change in a slope of the detector response value over time, a threshold change in a slope of the detector response value over time, or any combination thereof.

In one exemplary embodiment, the methods of the present invention comprise the step of generating a detector signal from at least one detector, the detector signal being generated in response to (i) the slope of a detector response as a function of time (i.e., the first derivative of a detector response), (ii) a change in the slope of the detector response as a function of time (i.e., the second derivative of the detector response), (iii) optionally, a threshold detector response value, or (iv) any combination of (i) to (iii) with desired combinations comprising at least (i) or at least (ii). In this exemplary embodiment, a substance is recognized from the shape of the detector response, specifically the first and/or second derivative of the detector response over time (i.e., slope and change in slope, respectively). In particular, a computer program analyzes the time sequence of detector response values and measures its rate of change (i.e., the first derivative), and the rate of the rate of change (i.e., the second derivative). When both the first derivative and the second derivative are increasing, a substance is beginning to be detected. Similarly, when both the first derivative and the second derivative are decreasing, the substance is ceasing to be detected.

Real-world detector values are typically noisy (e.g., jagged), so it is desirable to utilize low-pass numerical filtering (e.g., smoothing) over time. Consequently, the step of generating a detector signal from at least one detector desirably further comprises low-pass numerical filtering of (i) slope data over time, (ii) change in slope data over time, (iii) optionally, a threshold detector response value, or (iv) any combination of (i) to (iii) to distinguish actual changes in (i) slope data over time, (ii) change in slope data over time, (iii) optionally, a threshold detector response value, or (iv) any combination of (i) to (iii) from possible noise in the detector response. In desired embodiments, a finite impulse response (FIR) filter or infinite impulse response (IIR) filter may be utilized for low-pass numerical filtering of data over time (e.g., perhaps just an average of several samples). Typically, the decision algorithm utilizes a small number of sequential successes in time as confirmation of a real detector response/signal, and not noise.

In other embodiments, the method of analyzing a sample may comprise generating a composite signal comprising a detection response component from each detector, and collecting a new sample fraction in response to a change in the composite signal. In these embodiments, the step of generating a composite signal may comprise mathematically correlating (i) a detector response value, (ii) the slope of a given detector response as a function of time (i.e., the first derivative of a given detector response), (iii) a change in the slope of the given detector response as a function of time (i.e., the second derivative of the given detector response), or (iv) any combination of (i) to (iii) from each detector (i.e., each of the two or more detectors). For example, in some embodiments, the composite signal may comprise (i) the product of detector response values for each detector (i.e., each of two or more detectors) at a given time, (ii) the product of the first derivatives of the detector responses at a given time, (iii) the product of the second derivatives of the detector responses at a given time, or (iv) any combination of (i) to (iii).

In other embodiments in which a composite signal is used, the step of generating a composite signal may comprise mathematically correlating (i) a detector response value, (ii) the slope of a given detector response as a function of time (i.e., the first derivative of a given detector response), (iii) a change in the slope of the given detector response as a function of time (i.e., the second derivative of the given detector response), or (iv) any combination of (i) to (iii) from each sensor within a detector (i.e., n sensors observing a sample at n specific wavelengths) alone or in combination with any other detector responses present in the system. For example, in some embodiments, the composite signal may comprise (i) the product of detector response values for each sensor within a detector (i.e., n sensors observing a sample at n specific wavelengths) and any additional detector response values from other detectors (e.g., from an ELSD used in combination with an UV detector) at a given time, (ii) the product of the first derivatives of the detector responses for each sensor within a detector (i.e., n sensors observing a sample at n specific wavelengths) and any additional detector responses from other detectors at a given time, (iii) the product of the second derivatives of the detector responses for each sensor within a detector (i.e., n sensors observing a sample at n specific wavelengths) and any additional detector responses from other detectors at a given time, or (iv) any combination of (i) to (iii).

D. Collection of One or More Sample Fractions

The methods of the present invention may further comprise using a fraction collector, such as exemplary fraction collector 14 shown in FIGS. 1-3A and 4-9, to collect one or more sample fractions in response to one or more signals from at least one detector in a given liquid chromatography system. For example, in exemplary liquid chromatography systems 10, 20 and 30 shown in FIGS. 1, 2 and 3A respectively, methods of analyzing a sample may further comprise the step of collecting one or more sample fractions in response to one or more signals from first detector 13. In exemplary liquid chromatography systems 40, 50 and 60 shown in FIGS. 4, 5 and 6 respectively, methods of analyzing a sample may further comprise the step of collecting one or more sample fractions in response to one or more signals from first detector 13 (or first detector 131), second detector 16 (or second detector 161), or both first and second detectors 13 and 16 (or both first and second detectors 131 and 161).

In some embodiments of the present invention, the fraction collector is operatively adapted to recognize, receive and process one or more signals from at least one detector, and collect one or more sample fractions based on the one or more signals. In other embodiments, additional computer or microprocessing equipment is utilized to process one or more signals from at least one detector and subsequently provide to the fraction collector a recognizable signal that instructs the fraction collector to collect one or more sample fractions based on one or more signals from the additional computer or microprocessing equipment.

As discussed above, system components may be positioned within a given liquid chromatography system to provide one or more system properties. For example, at least one detector may be positioned within a given liquid chromatography system so as to minimize any time delay between (i) the detection of a given detector response and (ii) the step of collecting a sample fraction based on a signal generated from the detector response. In exemplary embodiments of the present invention, the liquid chromatography system desirably exhibits a maximum time delay of a given detector signal to the fraction collector (i.e., the time delay between (i) the detection of a given detector response and (ii) the step of collecting a sample fraction based on a signal generated from the detector response) of less than about 2.0 seconds (s) (or less than about 1.5 s, or less than about 1.0 s, or less than about 0.5 s).

In exemplary embodiments of the present invention utilizing two or more detectors or at least one detector comprising n sensors (as described above), the liquid chromatography system desirably exhibits a maximum time delay for any detector signal from any detector to the fraction collector (i.e., the time delay between (i) the detection of a given detector response and (ii) the step of collecting a sample fraction based on a signal (e.g., single or composite signal) generated from the detector response) of less than about 2.0 s (or less than about 1.5 s, or less than about 1.0 s, or less than about 0.5 s).

E. Sample Component(s) Separation Step

The methods of the present invention utilize a liquid chromatography (LC) step to separate compounds within a given sample. Depending on the particular sample, various LC columns, mobile phases, and other process step conditions (e.g., feed rate, gradient, etc.) may be used.

A number of LC columns may be used in the present invention. In general, any polymer or inorganic based normal phase, reversed phase, ion exchange, affinity, hydrophobic interaction, hydrophilic interaction, mixed mode and size exclusion columns may be used in the present invention. Exemplary commercially available columns include, but are not limited to, columns available from Grace Davison Discovery Sciences under the trade names VYDAC®, GRACERESOLV™, DAVISIL®, ALLTIMA™, VISION™, GRACEPURE™, EVEREST®, and DENALI®, as well as other similar companies.

A number of mobile phase components may be used in the present invention. Suitable mobile phase components include, but are not limited to, acetonitrile, dichloromethane, ethyl acetate, heptane, acetone, ethyl ether, tetrahydrofuran, chloroform, hexane, methanol, isopropyl alcohol, water, ethanol, buffers, and combinations thereof.

F. User Interface Steps

The methods of analyzing a sample in the present invention may further comprise one or more steps in which an operator or user interfaces with one or more system components of a liquid chromatography system. For example, the methods of analyzing a sample may comprise one or more of the following steps: inputting a sample into the liquid chromatography system for testing; adjusting one or more settings (e.g., flow or pressure settings, wavelengths, etc.) of one or more components within the system; programming at least one detector to generate a signal based on a desired mathematical algorithm that takes into account one or more detector responses from one or more sensors and/or detectors; programming one or more system components (other than a detector) to generate a signal based on a desired mathematical algorithm that takes into account one or more detector responses; programming a fraction collector to recognize a signal (e.g., a single or composite signal) from at least one detector, and collect one or more sample fractions based on a received signal; programming one or more system components (other than a fraction collector) to recognize an incoming signal from at least one detector, convert the incoming signal into a signal recognizable and processible by a fraction collector so that the fraction collector is able to collect one or more sample fractions based on input from the one or more system components; and activating or deactivating one or more system components (e.g., a tee valve, a splitter pump, a shuttle valve or a detector) at a desired time or in response to some other activity within the liquid chromatography system (e.g., a detector response displayed to the operator or user).

II. Apparatus for Analyzing Samples

The present invention is also directed to an apparatus and apparatus components capable of analyzing a sample or capable of contributing to the analysis of a sample using one or more of the above-described method steps.

As described above, in some exemplary embodiments of the present invention, an apparatus for analyzing a sample may comprise (i) a chromatography column; (ii) a tee having a first inlet, a first outlet and a second outlet; (iii) a fraction collector in fluid communication with the first outlet of the tee; (iv) a first detector in fluid communication with the second outlet of the tee; and (v) a splitter pump positioned in fluid communication with the second outlet of the tee and the first detector with the splitter pump being operatively adapted to actively control fluid flow to the first detector. In other exemplary embodiments of the present invention, a shuttle valve may be used in place of a tee/splitter pump combination to actively control fluid flow to the first detector.

Although not shown in FIGS. 1-9, any of the above-described apparatus (e.g., exemplary liquid chromatography systems 10 to 90) or apparatus components may further comprise system hardware that enables (i) the recognition of a detector response value or a change in a detector response value, (ii) the generation of a single from the detector response value or a change in a detector response value, (iii) the sending of a signal to one or more system components, (iv) the recognition of a generated signal by a receiving component, (v) processing of the recognized signal within the receiving component, and (vi) the initiation of a process step of the receiving component in response to the recognized signal.

In one embodiments, the apparatus (e.g., exemplary liquid chromatography systems 10 to 90) or a given apparatus component may further comprise system hardware that enables a first detector to send an activation signal to a splitter pump or a shuttle valve to (i) activate the splitter pump or shuttle valve, (ii) deactivate the splitter pump or shuttle valve, (iii) change one or more flow or pressure settings of the splitter pump or shuttle valve, or (iv) any combination of (i) to (iii). Suitable flow and pressure settings may include, but are not limited to, (i) a valve position, (ii) splitter pump or shuttle valve pressure, (iii) air pressure to a valve, or (iv) any combination of (i) to (iii).

In some embodiments, a splitter pump may be positioned between a tee and a first detector (see, for example, splitter pump 15 positioned between tee 12 and first detector 13 in FIG. 1). In other embodiments, a first detector may be positioned between a tee and the splitter pump (see, for example, first detector 13 positioned between tee 12 and splitter pump 15 in FIG. 2).

In other exemplary embodiments, the apparatus of the present invention comprise (i) a chromatography column; (ii) two or more detectors; and (iii) a fraction collector in fluid communication with the two or more detectors with the fraction collector being operatively adapted to collect one or more sample fractions in response to one or more detector signals from the two or more detectors. In some embodiments, the two or more detectors comprise two or more non-destructive detectors (e.g., two or more UV detectors) with no destructive detectors (e.g., mass spectrometer) in the system.

When two or more detectors are present, a splitter pump or shuttle valve may be used to split a volume of fluid flow between a first detector and a second detector. In other embodiments, a splitter pump or shuttle valve may be used to initiate or stop fluid flow to one detector in response to a detector response from another detector. In addition, multiple splitter pumps and/or shuttle valves may be used in a given system to actively control fluid flow to two or more detectors.

As discussed above, the apparatus may further comprise system hardware that enables generation of a detector signal from one or more detector responses. In one exemplary embodiment, the apparatus comprises system hardware that enables generation of a detector signal that is generated in response to (i) the slope of a detector response as a function of time (i.e., the first derivative of a detector response), (ii) a change in the slope of the detector response as a function of time (i.e., the second derivative of the detector response), (iii) optionally, a threshold detector response value, or (iv) any combination of (i) to (iii) with desired combinations comprising at least (i) or at least (ii). The system hardware desirably further comprises low-pass numerical filtering capabilities for filtering (i) slope data, (ii) change in slope data, (iii) optionally, a threshold detector response value, or (iv) any combination of (i) to (iii) over time to distinguish actual changes in (i) slope data, (ii) change in slope data, (iii) optionally, a threshold detector response value, or (iv) any combination of (i) to (iii) from possible noise in a given detector response.

In multi-detector systems, system hardware may also be used to enable the generation of a composite signal comprising a detection response component from each detector, as well as detection response components from multiple sensors within a given detector. In these embodiments, the system hardware is operatively adapted to send a command/signal to a fraction collector instructing the fraction collector to collect a new sample fraction in response to a change in the composite signal. The composite signal may comprise a mathematical correlation between (i) a detector response value, (ii) the slope of a given detector response as a function of time (i.e., the first derivative of a given detector response), (iii) a change in the slope of the given detector response as a function of time (i.e., the second derivative of the given detector response), or (iv) any combination of (i) to (iii) from each detector. For example, the composite signal may comprise (i) the product of detector response values for each detector at a given time, (ii) the product of the first derivatives of the detector responses at a given time, (iii) the product of the second derivatives of the detector responses at a given time, or (iv) any combination of (i) to (iii).

In one desired configuration, the apparatus for analyzing a sample comprising at least one detector operatively adapted to observe a sample at two or more specific optical wavelengths (e.g., within the UV spectrum), and system hardware that enables a fraction collector to collect a new sample fraction in response to (i) a change in a detector response at a first wavelength, (ii) a change in a detector response at a second wavelength, or (iii) a change in a composite response represented by detector responses at the first and second wavelengths. Each detector can operate at the same wavelength(s), at different wavelengths, or multiple wavelengths. Further, each detector may be in a parallel relationship with one another, in series with one another, or some combination of parallel and series detectors.

As discussed above, in one exemplary embodiment, the apparatus may comprise a single detector comprising n sensors operatively adapted to observe a sample at n specific optical wavelengths across a portion of or the entire UV absorbance spectrum (or any other portion of the absorbance spectrum using some other type of detector), and system hardware that enables a fraction collector to collect a new sample fraction in response to (i) a change in any one of the n detector responses at the n specific optical wavelengths, or (ii) a change in a composite response represented by the n detector responses.

When a splitter pump or shuttle valve is present to actively control fluid flow to at least one detector, the apparatus for analyzing a sample may further comprise system hardware that enables generation of an activation signal to the splitter pump or shuttle valve to (i) activate the splitter pump or shuttle valve, (ii) deactivate the splitter pump or shuttle valve, (iii) change one or more flow or pressure settings of the splitter pump or shuttle valve, or (iv) any combination of (i) to (iii). The activation signal may be generated, for example, by a system operator or by a system component, such as a detector (i.e., the activation signal being generated and sent by the detector in response to a detector response value or change in a detector response value of the detector as discussed above).

In an even further embodiment according to the present invention, an apparatus for analyzing a sample of fluid using chromatography includes a first fluid path of effluent from a chromatography column or cartridge; at least one detector that is capable of analyzing the sample of fluid; and a shuttle valve that transfers an aliquot sample of fluid from the first fluid path to the detector(s) without substantially affecting the flow properties of fluid through the first fluid path. The flow of the fluid through the first fluid path may be substantially laminar, due to the first fluid path or channel being substantially linear or straight through at least a portion of the valve. In a further exemplary embodiment, the pressure of the fluid through the first fluid path remains substantially constant and/or it does not substantially increase. In another embodiment, the flow rate of the fluid may be substantially constant through the first fluid path. In an alternative embodiment, a second fluid path is utilized to carry the aliquot sample of fluid from the shuttle valve to the detector(s). The flow of fluid through the second fluid path may be substantially laminar due to the second fluid path or channel being substantially linear or straight through at least a portion of the valve. In an exemplary embodiment, the pressure of fluid through the second fluid path is substantially constant and/or it does not substantially increase. In further embodiment, the flow rate of fluid may be substantially constant through the second fluid path.

In an even further exemplary embodiment, an apparatus for analyzing a sample of fluid using chromatography includes a first fluid path of effluent from a chromatography column; a second fluid path that carries the sample of fluid to at least one detector that is capable of analyzing the sample; and a shuttle valve that transfers an aliquot sample of fluid from the first fluid path to the second fluid path while maintaining a continuous second fluid path through the shuttle valve. In one embodiment, a continuous first flow path through the shuttle valve is maintained when the aliquot sample of fluid is removed from the first fluid path. In another embodiment, continuous first and second flow paths through the shuttle valve are maintained when the aliquot sample of fluid is removed from the first fluid path and transferred to the second fluid path.

In exemplary embodiments of the present invention, the apparatus for analyzing a sample further comprises a fraction collector that is operatively adapted to collect one or more sample fractions in response to one or more detector signals from (i) a first detector, (ii) a second detector (or any number of additional detectors), or (iii) both the first and second detectors (or any number of additional detectors). When multiple detectors are utilized, the apparatus may comprise a fraction collector operatively adapted to collect a new sample fraction in response to a change in a composite signal that accounts for one or more detector responses from each detector as described above.

As discussed above, in some exemplary embodiments, the apparatus for analyzing a sample comprises a fraction collector that is operatively adapted to recognize, receive and process one or more signals from at least one detector, and collect one or more sample fractions based on the one or more signals. In other embodiments, the apparatus for analyzing a sample comprises additional computer or microprocessing equipment that is capable of processing one or more signals from at least one detector and converting an incoming signal into a signal that is recognizable by the fraction collector. In this later embodiment, the fraction collector collects one or more sample fractions based on the one or more signals from the additional computer or microprocessing equipment, not from signal processing components of the fraction collector.

It should be noted that any of the above-described exemplary liquid chromatography systems may comprise any number of detectors, splitter pumps, tees, and shuttle valves, which may be strategically placed within a given system to provide one or more system properties. For example, although not shown in exemplary liquid chromatography system 60 in FIG. 6, an additional detector could be positioned between column 11 and shuttle valve 151 and/or between shuttle valve 151 and detector 161. Although not shown in exemplary liquid chromatography system 70 in FIG. 7, an additional detector could be positioned between column 11 and shuttle valve 151 and/or between shuttle valve 151 and shuttle valve 171 and/or between shuttle valve 171 and fraction collector 14. Additional detectors may be similarly positioned within exemplary liquid chromatography systems 80 and 90 shown in FIGS. 8 and 9 respectively, A number of commercially available components may be used in the apparatus of the present invention as discussed below.

A. Chromatography Columns

Any known chromatography column may be used in the apparatus of the present invention. Suitable commercially available chromatography columns include, but are not limited to, chromatography columns available from Grace Davison Discovery Sciences (Deerfield, Ill.) under the trade designations GRACEPURE™, GRACERESOLV™, VYDAC® and DAVISIL®.

B. Detectors

Any known detector may be used in the apparatus of the present invention. Suitable commercially available detectors include, but are not limited to, UV detectors available from Ocean Optics (Dunedin, Fla.) under the trade designation USB 2000™; evaporative light scattering detectors (ELSDs) available from Grace Davison Discovery Sciences (Deerfield, Ill.) under the trade designation 3300 ELSD™; mass spectrometers (MSs) available from Waters Corporation (Milford, Mass.) under the trade designation ZQ™; condensation nucleation light scattering detectors (CNLSDs) available from Quant (Blaine, Minn.) under the trade designation QT-500™; corona discharge detectors (CDDs) available from ESA (Chelmsford, Mass.) under the trade designation CORONA CAD™; refractive index detectors (RIDs) available from Waters Corporation (Milford Mass.) under the trade designation 2414; and fluorescence detectors (FDs) available from Laballiance (St. Collect, Pa.) under the trade designation ULTRAFLOR™.

In some embodiments, a commercially available detector may need to be modified or programmed or a specific detector may need to be built in order to perform one or more of the above-described method steps of the present invention.

C. Splitter Pumps

Any known splitter pump may be used in the apparatus of the present invention. Suitable commercially available splitter pumps include, but are not limited to, splitter pumps available from KNF (Trenton, N.J.) under the trade designation LIQUID MICRO™.

D. Shuttle Valves

Any known shuttle valve may be used in the apparatus of the present invention. Suitable commercially available shuttle valves include, but are not limited to, shuttle valves available from Valco (Houston, Tex.) under the trade designation CHEMINERT™, Rheodyne® shuttle valve available from Idex Corporation under the trade name MRA® and a continuous flow shuttle valve as described herein.

E. Fraction Collectors

Any known fraction collector may be used in the apparatus of the present invention. Suitable commercially available fraction collectors include, but are not limited to, fraction collectors available from Gilson (Middleton, Wis.) under the trade designation 215.

In some embodiments, a commercially available fraction collector may need to be modified and/or programmed or a specific fraction collector may need to be built in order to perform one or more of the above-described method steps of the present invention. For example, fraction collectors that are operatively adapted to recognize, receive and process one or more signals from at least one detector, and collect one or more sample fractions based on the one or more signals are not commercially available at this time.

III. Computer Software

The present invention is further directed to a computer readable medium having stored thereon computer-executable instructions for performing one or more of the above-described method steps. For example, the computer readable medium may have stored thereon computer-executable instructions for: adjusting one or more settings (e.g., flow settings, wavelengths, etc.) of one or more components within the system; generating a signal based on a desired mathematical algorithm that takes into account one or more detector responses; recognizing a signal from at least one detector; collecting one or more sample fractions based on a received signal; recognizing an incoming signal from at least one detector, convert the incoming signal into a signal recognizable and processible by a fraction collector so that the fraction collector is able to collect one or more sample fractions based on input from the one or more system components; and activating or deactivating one or more system components (e.g., a tee valve, a splitter pump, a shuttle valve, or a detector) at a desired time or in response to some other activity within the liquid chromatography system (e.g., a detector response).

IV. Applications/Uses

The above-described methods, apparatus and computer software may be used to detect the presence of one or more compounds in a variety of samples. The above-described methods, apparatus and computer software find applicability in any industry that utilizes liquid chromatography including, but not limited to, the petroleum industry, the pharmaceutical industry, analytical labs, etc.

EXAMPLES

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

In this example, the flash REVELERIS™ system (available from Grace Davison Discovery Sciences) was utilized. 4 mL of a mixture containing sucrose and aspirin was injected into a 4 g GRACERESOLV™ C18 flash column (available from Grace Davison Discovery Sciences), which was mounted in the flash system. A 50/50 methanol/water mobile phase was pumped through the system using an ALLTECH® model 300 LC pump. The column effluent was directed to a KNF splitter pump that diverted 300 uL/min of the column effluent to an ALLTECH® 3300 ELSD. The balance of the effluent flowed through an Ocean Optics UV detector to a Gilson fraction collector.

The sucrose and aspirin were separated on the flash column. Both the sucrose and the aspirin were detected by the ELSD. The UV detector only detected the aspirin. Both detectors responded to the aspirin at the same time. The fraction collector deposited the sucrose and aspirin in separate collection vials in response to a composite signal from the UV and ELSD detectors.

Example 2

In this example, the flash REVELERIS™ system (available from Grace Davison Discovery Sciences) was utilized. 4 mL of a mixture containing dioctyl phthalate and butyl paraben was injected into a 4 g GRACERESOLV™ C18 flash cartridge (available from Grace Davison Discovery Sciences), which was mounted in the flash system. A 80/20 methanol/water mobile phase was pumped through the system using an ALLTECH® model 300 LC pump. The column effluent was directed to a shuttle valve as described herein that diverted 300 uL/min of the column effluent to an ALLTECH® 3300 ELSD. The balance of the effluent flowed through an Ocean Optics UV detector to a Gilson fraction collector.

Figure 11:
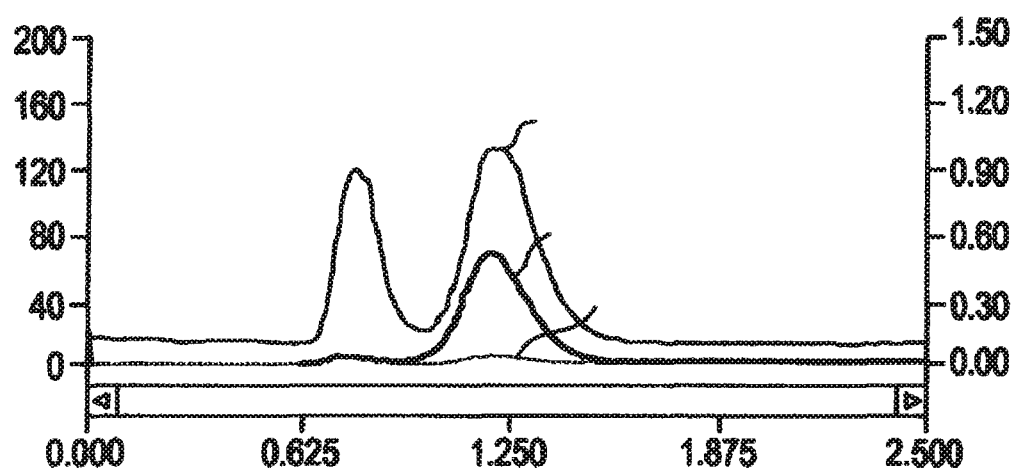
FIG. 11 depicts a chromatogram produced from the separation of a two component mixture using an exemplary chromatography system of the present invention.

This two component mixture contains a non-chromaphoric compound (one that does not absorb UV light) and a chromaphoric compound. The non-chromaphoric compound elutes from the flash cartridge first. FIG. 11 depicts a chromatogram that illustrates only the ELSD identifies all the components in the sample, as is evidenced by the two peaks on the chromatogram. The UV detector does not identify the non-chromaphoric compound (identified as the first peak by the ELSD), even at two wavelengths. Only the ELSD signal will be able to properly control the fraction collector, capturing both compounds. If the UV detector drove the fraction collector, (as would be the case in conventional Flash systems), the first compound would be sent to waste or improperly deposited in collection vessels without knowledge that these fractions contained desired sample. In conventional flash instruments, all fractions are screened by thin layer chromatography (TLC) after the chromatographic separation to find compounds that the UV detector may not have identified. This Example demonstrates that flash instruments equipped with an ELSD according to the present invention are able to identify and separate both chromaphoric and non-chromaphoric compounds, and postseparation TLC screening is not required.

While the invention has been described with a limited number of embodiments, these specific embodiments are not intended to limit the scope of the invention as otherwise described and claimed herein. It may be evident to those of ordinary skill in the art upon review of the exemplary embodiments herein that further modifications, equivalents, and variations are possible. All parts and percentages in the examples, as well as in the remainder of the specification, are by weight unless otherwise specified. Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 3%, 4%, 5% . . . 50%, 51%, 52%. . . 95%, 96%, 97%, 98%, 99%, or 100%. Moreover, any numerical range represented by any two values of R, as calculated above is also specifically disclosed. Any modifications of the invention, in addition to those shown and described herein, will become apparent to those skilled in the art from the foregoing description and accompanying drawings. Such modifications are intended to fall within the scope of the appended claims. All publications cited herein are incorporated by reference in their entirety.

What is claimed is:

1. A method of detecting and collecting one or more sample components within a sample stream in a chromatography system during a chromatographic run comprising:
   generating a first signal during the chromatographic run from at least one destructive detector, including at least one evaporative particle detector;
   generating a second signal during the chromatographic run from at least one non-destructive detector,
      wherein said non-destructive detector monitors a whole absorbance spectrum or a portion thereof comprising more than one wavelength, and wherein said second signal comprises at least one response value from each of the more than one wavelength; and
   collecting the one or more components from the stream in a fraction collector during the chromatographic run in response to a change in at least one of said signals during said chromatographic run.

2. The method of claim 1, wherein each signal comprises:
   (i) detector response values for the respective generating detector at a given time,
   (ii) the first derivatives of detector response values at a given time,
   (iii) the second derivatives of said detector response values at a given time, or
   (iv) any combination of (i) to (iii).

3. The method of claim 1, including at least one destructive detector selected from the group consisting of evaporative light scattering detectors (ELSD), mass spectrometers (MS), condensation nucleation light scattering detectors (CNLSD), and corona discharge detectors.

4. The method of claim 1, including at least one non-destructive detector selected from the group consisting of optical absorbance detectors, refractive index detectors (RID), fluorescence detectors (FD), chiral detectors (CD), and conductivity detectors.

5. The method of claim 1, wherein the non-destructive detector comprises at least one optical absorbance detector.

6. The method of claim 5, wherein the optical absorbance detector observes two or more optical wavelengths so as to produce two or more detector response values.

7. The method of claim 1, wherein the evaporative particle detector comprises an evaporative light scattering detector.

8. The method of claim 1, wherein the evaporative particle detector comprises an evaporative light scattering detector and the non-destructive detector comprises at least one optical absorbance detector.

9. The method of claim 1, further comprising:
   actively controlling fluid flow to the at least one destructive detector via
   a splitter pump;
   a shuttle valve; or
   a combination of a splitter pump and a shuttle valve;
      wherein the splitter pump, the shuttle valve, or the combination are in fluid communication with the at least one destructive detector.

10. The method of claim 9, wherein said actively controlling step comprises moving an aliquot to said destructive detector at a frequency of at least 1 aliquot every 10 seconds.

11. A non-transitory computer readable medium having stored thereon computer executable instructions for performing the method of claim 1.

12. An apparatus for detecting a sample using the method of claim 1.

13. A chromatographic apparatus for detecting and collecting one or more components within a sample stream during a chromatographic run comprising:
   at least one destructive detector, including at least one evaporative particle detector, to generate a response value during a chromatographic run;
   at least one non-destructive detector, wherein said non-destructive detector monitors a whole absorbance spectrum or a portion thereof comprising more than one wavelength during a chromatographic run and generates at least one response values from each of the more than one wavelength;
   a processor to receive said response values and to generate a first signal from the response value received from said destructive detector and to generate a second signal from the at least one response value received from said non-destructive detector; and
   a fraction collector to collect at least one fraction corresponding to one of said components in response to a change in at least one of said signals during said chromatographic run.

14. The apparatus of claim 13, wherein each signal comprises:
   (i) detector response values for the respective generating detector at a given time,
   (ii) the first derivatives of said detector response values at a given time,
   (iii) the second derivatives of said detector response values at a given time, or
   (iv) any combination of (i) to (iii).

15. The apparatus of claim 13, including at least one destructive detector selected from the group consisting of evaporative light scattering detectors (ELSD), mass spectrometers (MS), condensation nucleation light scattering detectors (CNLSD), and corona discharge detectors.

16. The apparatus of claim 13, including at least one non-destructive detector selected from the group consisting of optical absorbance detectors, refractive index detectors (RID), fluorescence detectors (FD), chiral detectors (CD), and conductivity detectors.

17. The apparatus of claim 13, wherein the non-destructive detector includes at least one optical absorbance detector.

18. The apparatus of claim 17, wherein the optical absorbance detector is adapted to observe two or more optical wavelengths so as to produce two or more detector response values.

19. The apparatus of claim 13, wherein the evaporative particle detector comprises an evaporative light scattering detector.

20. The apparatus of claim 13, further comprising:
   a splitter pump;
   a shuttle valve; or
   a combination of a splitter pump and a shuttle valve;
      wherein the splitter pump, the shuttle valve, or the combination are in fluid communication with the at least one destructive detector.

* * * * *